(12) United States Patent
Stringfield et al.

(10) Patent No.: US 10,339,648 B2
(45) Date of Patent: Jul. 2, 2019

(54) QUANTITATIVE PREDICTORS OF TUMOR SEVERITY

(71) Applicant: H. LEE MOFFITT CANCER CENTER AND RESEARCH INSTITUTE, INC., Tampa, FL (US)

(72) Inventors: Olya Stringfield, Tampa, FL (US); Robert J. Gillies, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 138 days.

(21) Appl. No.: 14/761,688

(22) PCT Filed: Jan. 21, 2014

(86) PCT No.: PCT/US2014/012309
§ 371 (c)(1),
(2) Date: Jul. 17, 2015

(87) PCT Pub. No.: WO2014/113786
PCT Pub. Date: Jul. 24, 2014

(65) Prior Publication Data
US 2015/0356730 A1    Dec. 10, 2015

Related U.S. Application Data

(60) Provisional application No. 61/754,140, filed on Jan. 18, 2013.

(51) Int. Cl.
*G06K 9/00* (2006.01)
*G06T 7/00* (2017.01)
(Continued)

(52) U.S. Cl.
CPC ......... *G06T 7/0012* (2013.01); *G01N 23/046* (2013.01); *G06T 5/50* (2013.01);
(Continued)

(58) Field of Classification Search
None
See application file for complete search history.

(56) References Cited

U.S. PATENT DOCUMENTS

2008/0170771 A1* 7/2008 Yamagata ............ G06F 19/321
382/128
2009/0257640 A1* 10/2009 Gossage ............ G06K 9/0014
382/133

(Continued)

OTHER PUBLICATIONS

Ball, JE. Level set-based core segmentation of mammographic masses facilitating three stage (core, periphery, spiculation) analysis. Proceedings of the 29th Annual International Conference of the IEEE EMBS, Lyon, France, 2007, pp. 819-824.

(Continued)

*Primary Examiner* — Fred H Hu
(74) *Attorney, Agent, or Firm* — Meunier Carlin & Curfman LLC

(57) ABSTRACT

Disclosed are methods for quantitatively predicting the severity of a tumor in a subject. In some embodiments, the methods further comprise selecting a course of therapy for the subject. In some embodiments, the tumor comprises is non-small cell lung cancer.

17 Claims, 16 Drawing Sheets

(51) Int. Cl.
    G06T 5/50      (2006.01)
    G01N 23/046    (2018.01)
    G06T 7/11      (2017.01)
    G06T 7/64      (2017.01)
(52) U.S. Cl.
    CPC ............. *G06T 7/11* (2017.01); *G06T 7/64* (2017.01); *G01N 2223/419* (2013.01); *G06T 2207/10081* (2013.01); *G06T 2207/20216* (2013.01); *G06T 2207/30061* (2013.01); *G06T 2207/30064* (2013.01); *G06T 2207/30096* (2013.01)

(56) References Cited

U.S. PATENT DOCUMENTS

| | | | |
|---|---|---|---|
| 2010/0111396 A1* | 5/2010 | Boucheron | G06K 9/0014 382/133 |
| 2011/0307838 A1* | 12/2011 | Dwyer | G06T 11/206 715/854 |
| 2012/0177280 A1 | 7/2012 | Zhukov et al. | |

OTHER PUBLICATIONS

Bhattacharjee, A et al. Classification of human lung carcinomas by mRNA expression profiling receals distinct adenocarcinoma subclasses. Proc Natl Acad Sci U S A, 2001. 98(24): pp. 13790-13795.

Diehn, M et al. Identification of noninvasive imaging surrogates for brain tumor gene-expression modules. Proc Acad Natl Sci U S A, 2008. 105(13): pp. 5213-5218.

Ding, L et al. Somatic mutations affect key pathways in lung adenocarcinoma. Nature, 2008. 455(7216): pp. 1069-1075.

Ganeshan, B et al. Texture analysis of non-small cell lung cancer on unenhanced computed tomography: initial evidence for a relationship with tumour glucose metabolism and stage. Cancer Imaging, 2010. 10: pp. 137-143.

Ganeshan, B et al. Tumour heterogeneity in non-small cell lung carcinoma assessed by CT texture analysis: a potential marker of survival. Eur Radiol, 2012. 22(4): pp. 796-802.

Gatenby, R.A., O. Grove, and R.J. Gillies, Quantitative Imaging in Cancer Evolution and Ecology. Radiology, 2013. 269(1):8-15.

Gevaert, O et al. Non-small cell lung cancer: identifying prognostic imaging biomarkers by leveraging public gene expression microarray data—methods and preliminary results. Radiology, 2012. 264(2): pp. 387-396.

Gillies RJ and Gatenby RA. Radiomics of NSCLC, QIN Progress Report, Moffitt Cancer Center, 2012.

Graves, EE et al. The tumor microenvironment in non-small-cell lung cancer. Semin Radiat Oncol, 2010. 20(3): p. 156-63.

Gu, Y et al. Automated Delineation of Lung Tumors from CT Images Using a Single Click Ensemble Segmentation Approach. Pattern Recognit, 2013. 46(3): p. 692-02.

Honda, T et al. Radiographic and pathological analysis of small lung adenocarcinoma using the new IASLC classification. Clin Radiol, 2013. 68(1): p. e21-26.

Jaffe, CC. Imaging and genomics: is there a synergy? Radiology, 2012. 264(2): p. 329-31.

Jia, G et al. Colorectal liver metastases: contrast agent diffusion coefficient for quantification of contrast enhancement heterogeneity at MR imaging. Radiology, 2008. 248(3): p. 901-9.

Kumar, V et al. Qin Radiomics: The Process and the Challenges. Magn Reson Imaging, 2012, 30(9), 1234-1248.

Lardinois, D et al. Staging of non-small-cell lung cancer with integrated positron-emission tomography and computed tomography. N. Engl J Med, 2003. 348(25): p. 2500-7.

Miles, KA et al. Colorectal cancer: texture analysis of portal phase hepatic CT images as a potential marker of survival. Radiology, 2009. 250(2): p. 444-52.

Nair, VS et al. PET scan 18F-fluorodeoxyglucose uptake and prognosis in patients with resected clinical stage IA non-small cell lung cancer. Chest, 2010. 137(5): p. 1150-6.

Nair VS et al. Prognostic PET 18F-FDG uptake imaging features are associated with major oncogenomic alterations in patients with resected non-small cell lung cancer. Cancer Res, 2012. 72(15): p. 3725-34.

Peifer, M et al. Integrative genome analyses identify key somatic driver mutations of small-cell lung cancer. Nat Genet, 2012. 44(10): p. 1104-10.

Rees, JH et al. Glioblastoma multiforme: radiologic-pathologic correlation. Radiographics, 1996. 16(6): p. 1413-38.

Rose, CJ et al. Quantifying spatial heterogeneity in dynamic contrast-enhanced MRI parameter maps. Magn Reson Med, 2009. 62(2): p. 488-99.

Rubin, DL et al. A semantic image annotation model to enable integrative translational research. Summit on Translat Bioinforma, 2009. 2009: p. 106-10.

Rutman, AM and Kuo, MD. Radiogenomics: creating a link between molecular diagnostics and diagnostic imaging. Eur J Radiol, 2009. 70(2): p. 232-41.

Segal, E et al. Decoding global gene expression programs in liver cancer by noninvasive imaging. Nat Biotechnol, 2007. 25(6): p. 675-80.

Siegel, R et al. Cancer statistics, 2013. CA Cancer J Clin, 2013. 63(1): p. 11-30.

Tixier, F et al. Intratumor heterogeneity characterized by textural features on baseline 18F-FDG PET images predicts response to concomitant radiochemotherapy in esophageal cancer. J Nucl Med, 2011. 52(3): p. 369-78.

Yang, X and Knopp, MV. Quantifying tumor vascular heterogeneity with dynamic contrast-enhanced magnetic resonance imaging: a review. J Biomed Biotechnol, 2011. 2011: p. 732848.

International Search Report and Written Opinion dated Jun. 18, 2014, in related International Application No. PCT/US14/12309.

International Preliminary Report on Patentability dated Jul. 30, 2014, in related International Application No. PCT/US14/12309.

Curado et al., Cancer Incidence in Five Continents. IARC Scientific Publications, Lyon, 2007, 8(160).

* cited by examiner

QUANTITATIVE PREDICTORS OF TUMOR SEVERITY

CROSS-REFERENCE TO RELATED APPLICATIONS

This application claims benefit of U.S. Provisional Application No. 61/754,140, filed Jan. 18, 2013, which is hereby incorporated herein by reference in its entirety.

STATEMENT OF GOVERNMENT SUPPORT

This invention was made with government support under Grant No. CA143062 awarded by the National Cancer Institute at the National Institutes of Health. The government has certain rights in this invention.

TECHNICAL FIELD

This application relates generally to quantitative methods for predicting tumor severity from anatomical images.

BACKGROUND

Lung cancer continues to be the leading cause of cancer related deaths in the United States and worldwide. Despite advances made in understanding and treatment of the disease, the long-term survival rate has remained low. The overall 5-year survival rate is 15% and has not improved significantly over the past few decades.

The heterogeneity of histopathologic subtypes within lung cancer remains a major roadblock to understanding the origin and the course of the disease. The WHO 1996 classification identifies four major histopathological types of lung carcinomas: small cell, squamous cell, adenocarcinoma and large cell. The last three groups combined are referred to as non-small-cell lung cancers (NSCLC) and constitute approximately 80% of all lung cancers.

NSCLC is a heterogeneous group with variability in terms of histological composition, prognostic signatures, and clinical outcomes yet the histopathologic subtypes falling under the common NSCLC umbrella tend to be approached with a common therapeutic strategy. To date, the list of validated prognostic factors for NSCLC patients remains limited. Tumor Node and Metastasis (TNM) staging system and performance status are currently the only validated predictors for the disease, and development of additional prognostic biomarkers is critically needed. While TNM scoring is used to plan treatment and offers prognostic insight, there is a wide spectrum of treatment response and metastatic behavior in NSCLC patients with tumors within the same stages.

There were 228,000 estimated cases of new lung and bronchus cancer is 2013, and approximately 40% of these were patients diagnosed with lung adenocarcinoma. An estimated 20% of new NSCLC adenocarcinoma cases are Stage I patients as determined by current staging systems. Stage I patients are typically not given adjuvant chemotherapy post surgery, while most stage II and III patients are. Unlike other types of cancer, where early diagnosis has significant survival advantages, some 35% to 45% of people with stage I lung cancer die within five years due to recurrent disease, despite successfully surgery.

SUMMARY

Disclosed herein are systems and methods for quantitatively predicting the severity of a tumor in a subject. The methods first involve acquisition of an anatomical image of a region of interest in a subject containing a tumor. The anatomical image can then be segmented to define a volume of interest representing the tumor. One or more image features can then be extracted from the anatomical or segmented image. In particular embodiments, the image features can be selected from the group consisting of convexity, entropy, or a combination thereof. The disclosed methods can then involve generating a quantitative score that is associated with tumor severity for each of the one or more image features.

Suitable anatomical imaging techniques include those that can discern one or more of the size, shape, and internal heterogeneity of a tumor. For example, the anatomical images can be acquired by computed tomography. The anatomical image can be either a two-dimensional image, a stack of two-dimensional image slices, or a rendered three-dimensional image of the region of interest.

In some embodiments, the quantitative score is a ratio of the average entropy in a core region of the segmented image and the average entropy in a boundary region of the segmented image. For example, the ratio can be calculated by an algorithm that performs the steps comprising: subdividing the segmented image into the core region and the boundary region; calculating an entropy coefficient for each pixel in the core region and the boundary region; averaging the entropy coefficients for the core region and the boundary region; and comparing the average entropy coefficient of the core region to the average entropy of the boundary region to obtain the entropy ratio.

In some embodiments, the convexity is calculated by an algorithm that performs steps comprising: identifying a border of the segmented image; creating a mask of the segmented image; calculating the area of the mask of the segmented image; creating a convex hull of the border of the segmented image; calculating the area of the convex hull; and comparing the area of the mask to the area of the convex hull to calculate convexity.

In some embodiments, the algorithm for convexity further comprises correcting for overlap with another structure, such as for example a NSCLC adenocarcinoma overlapping with the pleural wall. For example, the correction can comprise: identifying a border of a structure; comparing the border of the structure with the border of the sample area to determine overlap between the sample area and the structure; and eliminating overlapping regions from the area of the mask of the sample area and the area of the convex hull used to calculate convexity.

In some embodiments, the quantitative score for convexity is calculated as the average of the convexity for each two-dimensional image slice in a three-dimensional stack. For example, the algorithm for convexity can further comprise eliminating from the two-dimensional slices used to compute the average convexity score any two-dimensional slice that overlaps with the structure.

The disclosed systems and methods can be combined with existing staging systems to improve diagnosis and prognosis of a tumor. For example, where the tumor is a breast cancer, the method can be combined with a tumor node metastasis (TNM) staging system to predict the severity of the tumor.

In some embodiments, the methods further comprise selecting a course of therapy for the subject based on the quantitative score for the one or more image features. In some embodiments, the quantitative score for entropy is an indication of tumor density, wherein the method further comprises selecting adjuvant therapy for the subject if the quantitative score for entropy indicates a high tumor density.

In some embodiments, the quantitative score for convexity is an indication of either an irregular or convex tumor shape, wherein the method comprises selecting adjuvant therapy for the subject if the quantitative score for convexity indicates an irregular tumor shape.

The disclosed systems and methods can be adapted for use with any solid tumor where shape and/or tumor density is a predictor of prognosis. For example, in some embodiments, the tumor is a non-small cell lung cancer, such as lung adenocarcinoma.

Also disclosed is a computer system comprising memory on which is stored instructions to perform the disclosed methods. For example, the memory can contain instructions to receive anatomical images acquired from a region of interest in a subject containing a tumor, segment the anatomical image to define a volume of interest representing the tumor, extract one or more image features from the segmented image, and generate a quantitative score for the one or more image features. In some embodiments, the image features are selected from the group consisting of entropy, convexity, or a combination thereof. In some embodiments, the quantitative score for the one or more image features can be associated with tumor severity.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
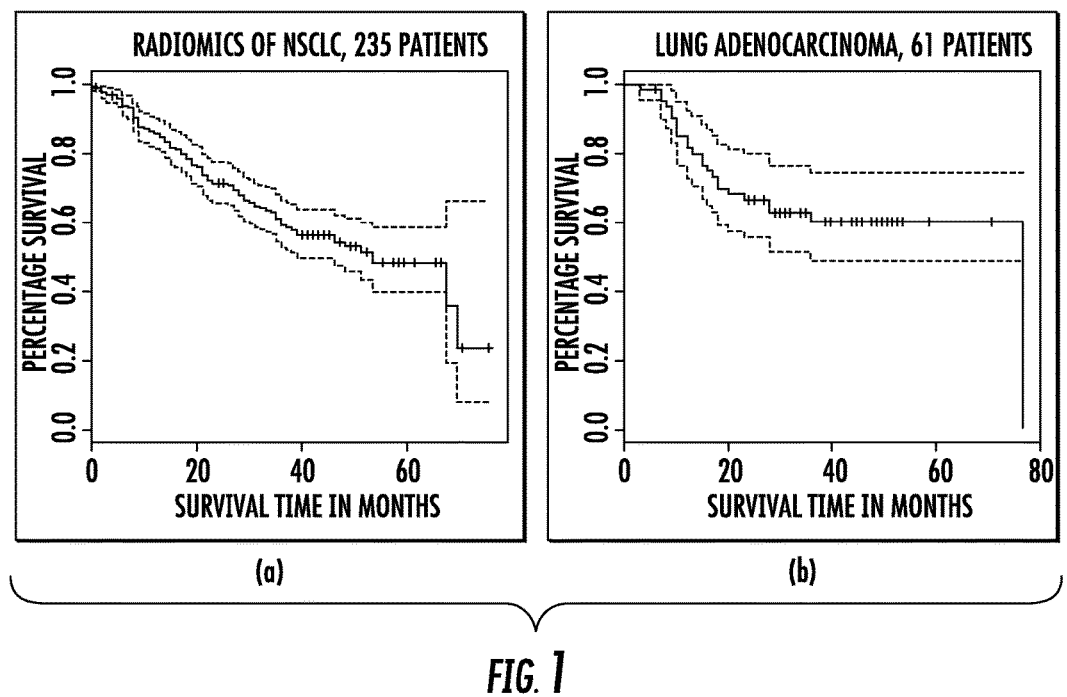
FIG. 1 depicts the overall survival plot of (a) the entire cohort and (b) the adenocarcinoma sub-cohort.

Radiomics involves the high throughput extraction of quantitative imaging features, which can be used to create mineable databases from radiological images. Such profound analyses and mining of image feature data can reveal quantitative predictive or prognostic associations between images and medical outcomes. In cancer, current radiological practice is generally qualitative. When quantitative, measurements are commonly limited to dimensional measurements of tumor size via one (RECIST) or two (WHO) dimensional long axis measures. These measures do not reflect the complexity of tumor morphology or behavior, nor, in many cases, are changes in these measures predictive of therapeutic benefit. When additional quantitative measures are obtained, they generally average values over an entire region of interest (ROI).

There are efforts to develop a standardized lexicon for the description of such lesions, and to include these descriptors via annotated Image Markup (AIM) into quantitative, mineable data. However, such approaches do not completely cover the range of quantitative features that can be extracted from images, such as texture, shape, or margin gradients. Texture features can provide significantly higher prognostic power than ROI-based methods. In the current iteration of radiomics, image features may be extracted automatically and with high throughput, putting a high premium on machine learning algorithm development.

One of the goals of radiomics is to convert images into mineable data, with high fidelity and high throughput. The radiomics enterprise can be divided into five processes with definable inputs and outputs, each with its own challenges that need to be overcome: (i) image acquisition and reconstruction; (ii) image segmentation and rendering (iii) feature extraction and feature qualification (iv) databases and data sharing; and (v) ad hoc informatic analyses. Each of these steps poses discrete challenges. For example, optimum protocols for image acquisition and reconstruction should be identified and harmonized. Segmentations should be robust and involve minimal operator input. Features should robustly reflect the complexity of the individual volumes, but should not be overly complex or redundant. Informatics databases that allow for incorporation of image features and image annotations, along with medical and genetic data should be generated. Finally, the statistical approaches to analyze these data should be optimized. Variation in results may come from variations in any of these individual processes.

Disclosed herein are methods for quantitatively predicting the severity of a tumor in a subject. The methods can comprise segmenting an anatomical image acquired from a region of interest in a subject containing the tumor, extracting one or more image features from the segmented image, and generating a quantitative score for the one or more image features, wherein the quantitative score is associated with tumor severity. In some embodiments, the method is combined with a tumor node metastasis (TNM) staging system to predict the severity of the tumor. In some embodiments, the methods further comprise selecting a course of therapy for the subject based on the quantitative score for the one or more image features.

Anatomical Imaging and Reconstruction

In some embodiments, the method further comprises the step of acquiring an anatomical image of a region of interest in a subject containing a tumor. Medical imaging, or anatomical imaging, is the technique and process used to create images of a subject's body (or parts and function thereof) for clinical purposes (e.g., medical procedures seeking to reveal, diagnose, or examine disease) or medical science (e.g., the study of normal anatomy and physiology). Suitable anatomical imaging techniques include those that can discern one or more of the size, shape, and internal heterogeneity of a tumor. Examples include, but are not limited to, radiology (which uses the imaging technologies of X-ray radiography such as computed tomography (CT)), magnetic resonance imaging (MRI), medical ultrasonography or ultrasound, endoscopy, elastography, tactile imaging, thermography, medical photography and nuclear medicine functional imaging techniques such as positron emission tomography (PET).

In routine clinical image acquisition there is wide variation in imaging parameters such as image resolution (pixel size or matrix size and slice thickness), washout period in the case of PET imaging, patient position, and the variations introduced by different reconstruction algorithms and slice thickness, which are different for each scanner vendor. Even this simple set of imaging issues can create difficulty in comparing results obtained across institutions with different scanners and patient populations. In addition, it is a challenge to identify and curate a large number of image data examples with similar clinical parameters such as disease stage.

Quantitative imaging with 2-deoxy-2-[18F]fluoro-D-glucose (18-FDG) PET scans is a challenge not only because it requires calibration of the scanner and standardization of the scan protocol but also requires the patient and staff to adhere to a strict patient protocol. From a technical viewpoint the main challenges are the dose calibration and the metabolic volume or VOI reconstruction that depends heavily on the scan protocol and source-to-background ratio. Before a scanner is used in a quantitative manner, inter-institution cross-calibration and quality control should be done. From a patient protocol perspective, administration issues (residual activity in syringe, paravenous administration), blood glucose level, uptake period, breathing, patient comfort and inflammation all influence the quantitation of the standardized uptake value (SUV) of 18-FDG. Complying with a strict protocol can be another prerequisite to quantitative PET imaging.

The signal intensities in magnetic resonance (MR) images arise from a complex interplay of inherent properties of the tissue, such as relaxation times and acquisition parameters. Certain techniques, such as diffusion weighted imaging (DWI) and dynamic contrast enhanced (DCE) MRI allow assessment of physiological properties of tissue. For example, the apparent water diffusion coefficient (ADC) determined using DWI varies inversely with tissue cellularity. DCE can be used to extract vascular flow, permeability and volume fractions. Although both of these techniques provide quantitative information, their reliability and reproducibility can depend on acquisition parameters and conditions. DWI images can be of low spatial resolution and can be sensitive to motion and magnetic susceptibility and the quantitation can be dependent on k-space trajectory, gradient strengths, and b-values. DWI has been proposed as a cancer imaging biomarker and there are efforts to develop quality control protocols. Results of the DCEMRI can depend on the contrast agent dose, method of administration, pulse sequence used, field strength of the scanner and the analysis method used.

Ideally, MR images will all have the same field of view, field strength and slice thickness. Where possible, e.g. brain tumors, multiple sequences with contrast enhancement such as T1-weighted, T2-weighted and FLAIR can be very useful. In magnetic resonance images of human brain tumors, radiomics has the potential to play an important role in categorizing the tumor. It is possible to view the tumor as having different regions using image features, including texture, wavelets, etc. For example, there will be areas of enhancement and potentially necrosis. The tumor bed can be extracted as an expanded region around the post contrast T1 weighted image, for example. Unsupervised clustering can be used to group the data into regions using data from multiple registered sequences. The extraction of image features from those regions, including such things as their location within the tumor bed, can allow for new types of tumor characterization. It has been observed that enhancement in individual tumors can be heterogeneous, and that analysis of this heterogeneity has prognostic value. The location and characteristics of such regions has the potential to provide new insights into tumor prognosis and how well it is likely to respond to targeted treatments. The opportunity to acquire images over time will allow for comparisons and contrasts between regions.

In some embodiments, the anatomical images are computed tomography images. Computed tomography (CT) is an imaging procedure that uses special x-ray equipment to create detailed pictures, or scans, of areas inside the body. It is also called computerized tomography and computerized axial tomography (CAT). Each picture created during a CT procedure shows the organs, bones, and other tissues in a thin "slice" of the body. In some embodiments, each slice can be examined individually (2-dimensional pictures), or they can be examined as a whole (a 3-dimensional picture that can be created by stacking the 2-dimensional pictures). Computer programs are used to create both types of pictures. In some embodiments, the anatomical image comprises a stack of two-dimensional image slices of the region of interest. In some embodiments, the method further comprises rendering the two-dimensional image slices into a three-dimensional image.

Of all the imaging modalities, CT can be straightforward and perhaps the easiest to compare across institutions and vendors. For example, standard "phantoms" exist that can be used to evaluate, analyze and tune the performance of various CT scanners. The imaging performance of a scanner will depend also on the imaging technique. As the slice thickness is reduced, the photon statistics within a slice are reduced unless the mA or kVp is increased. The axial field of view will also change the voxel size within a slice, and the reconstruction matrix size can also be varied from 512×512 up to 1024×1024 which also changes the voxel size. Although there can be some variation, different vendors of CT scanner have algorithms that are similar enough to be quantitatively comparable. Indeed the focus of the approach discussed herein is to use features with a) sufficient dynamic range between patients b) intrapatient reproducibility and c) insensitivity to image acquisition and reconstructions protocol.

CT can involve the use of a contrast (imaging) agent, or "dye." The dye may be given by mouth, injected into a vein, given by enema, or any combination thereof, before the procedure. The contrast dye highlights specific areas inside the body, resulting in clearer pictures. Iodine and barium are two dyes commonly used in CT.

Because contemporary CT scanners offer isotropic or near isotropic, resolution, display of images does not need to be restricted to conventional axial images. Instead, it is possible for a software program to build a volume by "stacking" the individual slices one on top of the other. The program may then display the volume in an alternative manner. Multiplanar reconstruction (MPR) is the simplest method of reconstruction. A volume can be built by stacking the axial slices. The software then cuts slices through the volume in a different plane (usually orthogonal). As an option, a special projection method, such as maximum-intensity projection (MIP) or minimum-intensity projection (mIP/MinIP), can be used to build the reconstructed slices. Modem software also allows reconstruction in non-orthogonal (oblique) planes so that the optimal plane can be chosen to display an anatomical structure. This may be particularly useful for visualizing the structure of the bronchi as these do not lie orthogonal to the direction of the scan. MIP reconstructions enhance areas of high radiodensity, and so are useful for angiographic studies. MIP reconstructions tend to enhance air spaces so are useful for assessing lung structure.

Other 3D rendering techniques can include surface rendering, volume rendering, image segmentation, or combinations thereof. In surface rendering, a threshold value of radiodensity is set by the operator (e.g., a level that corresponds to bone). From this, a three-dimensional model can be constructed using edge detection image processing algorithms and displayed on a screen. Multiple models can be constructed from various thresholds, allowing different colors to represent each anatomical component such as bone, muscle, and cartilage. However, the interior structure of each element is not visible in this mode of operation.

Edge detection is the name for a set of mathematical methods which aim at identifying points in a digital image at which the image brightness changes sharply or, more formally, has discontinuities. The points at which image brightness changes sharply are typically organized into a set of curved line segments termed edges. Edge detection is a fundamental tool in image processing, particularly in the areas of feature detection and feature extraction.

Surface rendering is limited in that it will display only surfaces that meet a threshold density, and will display only the surface that is closest to the imaginary viewer. In volume rendering, transparency, colors and shading are used to allow a better representation of the volume to be shown in a single image. For example, the bones of the pelvis could be displayed as semi-transparent, so that, even at an oblique angle, one part of the image does not conceal another.

Segmentation

Where different structures have similar radiodensity, it can become impossible to separate them simply by adjusting volume rendering parameters. The solution is called segmentation, a manual or automatic procedure that can remove the unwanted structures from the image. Image segmentation is the process of partitioning a digital image into multiple segments (sets of pixels, also known as superpixels). The goal of segmentation is to simplify and/or change the representation of an image into something that is more meaningful and easier to analyze. Image segmentation is typically used to locate objects and boundaries (lines, curves, etc.) in images. More precisely, image segmentation is the process of assigning a label to every pixel in an image such that pixels with the same label share certain visual characteristics.

The result of image segmentation is a set of segments that collectively cover the entire image, or a set of contours extracted from the image. Each of the pixels in a region is similar with respect to some characteristic or computed property, such as color, intensity, or texture. Adjacent regions are significantly different with respect to the same characteristic(s). When applied to a stack of images, typical in medical imaging, the resulting contours after image segmentation can be used to create 3D reconstructions with the help of interpolation algorithms.

Therefore, in some embodiments, the methods comprise segmenting an anatomical image acquired from a region of interest in a subject containing the tumor using a segmentation algorithm to define a volume of interest representing the tumor. Segmentation of images into volumes-of-interest (VOI) such as tumor, normal tissue and other anatomical structures for subsequent informatic analyses has previously been performed manually. However, manual segmentation even when performed by expert readers suffers from high inter-reader variability and is labor intensive; thus not feasible for radiomic analysis of very large data sets. Many automatic and semi-automatic segmentation methods have been developed across various image modalities like CT, PET and MRI and also for different anatomical regions like brain, breast, lung, liver etc. The segmentation method should be as automatic as possible with minimum operator interaction, time efficient and should provide accurate and reproducible boundaries.

Many popular segmentation algorithms have been applied in medical imaging studies, the most popular ones include region growing methods, level set methods, graph cut methods, active contours (snake) algorithms and semi-automatic segmentations such as livewires, etc.

Region growing algorithms are rapid, but undesired "regions" will be produced if the image contains too much noise. The level set method, by representing a contour as the zero level set of a higher dimensional function (level set function), formulates the motion of the contour as the evolution of the level set function. The graph cut method is relatively new in the area of image segmentation, which constructs an image-based graph and identifies a global optimum, it is computationally expensive. Another problem for graph cut is the over segmentation.

The active contours (snake) algorithm works like a stretched elastic band being released. The start points are defined around the object which needs to be extracted. The points then move through an iterative process to a point with the lowest energy function value. The active contours requires a good initialization, it is also sensitive to noise, which may lead the snake to undesired locations. The live wire (intelligent scissor) method is motivated by the general paradigm of the active contour algorithm: it converts the segmentation problem into an optimal graph search problem via local active contour analysis and its cost function is minimized by using dynamic programming. A problem with the live wire approach is that it is semi-automatic, requiring multiple human interactions. With proper parameters settings, each segmentation could segment the region of interest automatically or semi-automatically.

The segmentation of CT thorax images usually requires segmentation of lung fields for successive segmentation of lung nodules. Right and left lungs should be automatically segmented which may serve as a preprocessing step. This has been achieved relatively successfully, however, in cases where high intensity tumors are attached to the pleural wall or mediastinum, automatic segmentation often underperforms. Specifically, in such cases the rule-based methods can result in the false extension of lung boundaries into the mediastinum or heart.

Stage I and Stage II NSCLC nodules can often present as homogenous, high-intensity lesions on a background of low-intensity lung parenchyma. These can be segmented with high reproducibility and accuracy. However, partially solid, ground glass opacities (GGOs), nodules attached to vessels and nodules attached to the pleural wall remain difficult to segment automatically and show low reproducibility, especially for Stage III and Stage IV disease.

Imaging Features

In some embodiments, the methods comprise extracting one or more image features from the segmented image. In some embodiments, the image features are selected from the group consisting of convexity, entropy or a combination thereof. These features can describe characteristics of the tumor intensity histogram (e.g. high or low contrast), tumor shape (e.g. round or spiculated), texture patterns (e.g. homogeneous or heterogeneous), as well as descriptors of tumor location and relations with the surrounding tissues (e.g. near the heart).

Tumor intensity histogram-based features reduce the 3-dimensional data of a tumor volume in to a single histogram. This histogram describes the fractional volume for a selected structure for the range of voxel values (e.g. Hounsfield units for a CT scan, or standardized uptake values (SUV) for a FDG-PET scan). From this histogram, common statistics can be calculated (e.g. mean, median, min, max, range, skewness, kurtosis), but also more complex values, such as metabolic volume above an absolute SUV of 5 or the fraction of high density tissue measured with CT. Such threshold values have shown promise in developing classifier models, and optimum thresholds for a given task can be identified with receiver operator characteristic (ROC) analyses. As the outcome (e.g. time to recurrence) to which the threshold is being compared can also have a variable threshold, 3-D ROC approaches have been developed to represent a surface to optimize both the biomarker and the outcome thresholds.

Quantitative features describing the geometric shape of a tumor can also be extracted from the 3-dimensional surface of the rendered volumes. For example the total volume or surface area can be an important characteristic. Also, the surface to volume ratio can be determined, where a speculated tumor has a higher value than a round tumor with a similar volume. Furthermore, descriptors of tumor compactness and shape (sphericity etc.) can also be calculated.

Second order statistics or co-occurrence matrix features can be used for texture classification, and are widely applied in medical pattern recognition tasks. The basis of the co-occurrence features lies on the second-order joint conditional probability density function P(i,j;a,d) of a given texture image. The elements (i,j) of the co-occurrence matrix for the structure of interest represents the number of times that intensity levels i and j occur in two voxels separated by the distance (d) in the direction (a). Here, a matrix can be selected to cover the 26-connected directions of neighboring voxels in 3D space. The matrix size is dependent on the intensity levels within the 3D structure. Subsequently, from this conditional probability density function features can be extracted, e.g. describing autocorrelation, contrast, correlation, cluster prominence, cluster shade, cluster tendency, dissimilarity, energy, homogeneity, maximum probability, sum of squares, sum average, sum variance, sum entropy, or difference entropy, etc. Furthermore, gray level run length features, derived from run length matrices and using run length metrics can be extracted. A gray level run is the length, in number of pixels, of consecutive pixels that have the same gray level value. From the gray level run length matrix features can be extracted describing short and long run emphasis, gray level nonuniformity, run length non uniformity, run percentage, low gray level run emphasis, high gray level run emphasis. As expected, such analyses can generate hundreds of variables, some of which may be redundant. Thus it is important to assess the redundancy of these data using co-variance.

As described above, a dauntingly large number of image features may be computed. However, all these extracted features may not be useful for a particular task. In addition, the numbers of extracted features can be higher than the number of samples in a study, reducing power and increasing the probability of over-fitting the data. Therefore, dimensionality reduction and selection of task-specific features for best performance can be a necessary step. Different feature selection methods can be used for this purpose and may exploit machine learning or statistical approaches. Dimensionality reduction can also be achieved by combining or transforming the original features to obtain a new set of features by using methods like principal component analysis. In addition to feature selection for informative and non-redundant features, high reproducibility of the features is important in the development of clinical biomarkers, which can require the availability of a test-retest data set.

Entropy

Figure 20:
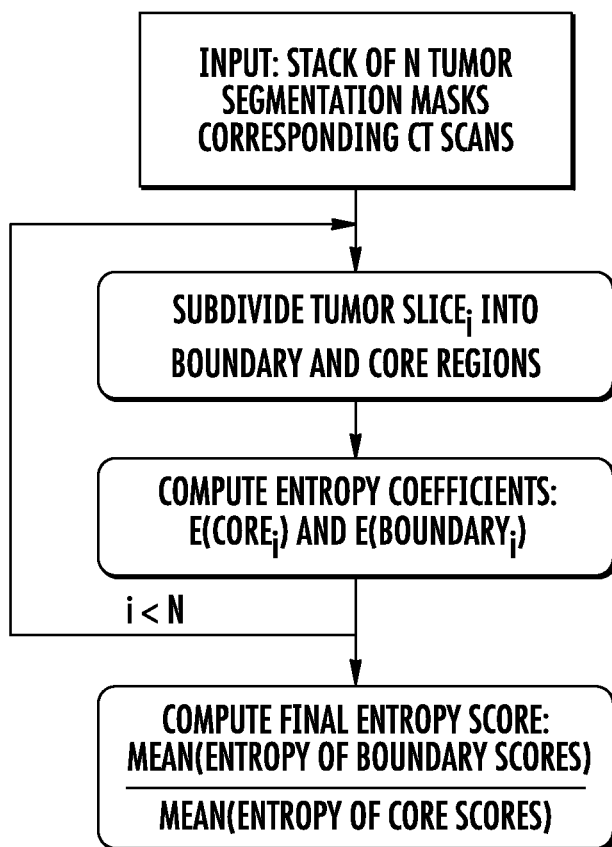
FIG. 20 is a schematic of an exemplary algorithm used to compute entropy.

In some embodiments, the image feature is entropy. Entropy in the image processing context is a texture-based statistical measure of the variation in the histogram distribution which reflects the predictability of intensity values within a given region of interest. In some embodiments, the quantitative score is a ratio of the average entropy in a core region of the segmented image and the average entropy in a boundary region of the segmented image. In some embodiments, the ratio is calculated by an algorithm that performs the steps comprising: subdividing the segmented image into the core region and the boundary region; calculating an entropy coefficient for each pixel in the core region and the boundary region; averaging the entropy coefficients for the core region and the boundary region; and comparing the average entropy coefficient of the core region to the average entropy of the boundary region to obtain the entropy ratio. This algorithm is further illustrated in FIG. 20.

In some examples, entropy coefficients can be computed within a sliding window surrounding it (e.g., 3×3, 5×5 or 7×7) as $-\text{sum}(p_i * \log 2(p_i))$ where $p_i$ represents the probability of the occurrence of the given intensity value, using a default histogram with 256 intensities. A coefficient is computed for each pixel, it is a measure of randomness, how predictable or not the intensity value of that pixel is. Entropy is a measure of attenuation heterogeneity in CT images.

In some examples for computing entropy, the original region of interest of the entire tumor can be subdivided into two distinct regions, such as the core and boundary regions. The entropy is computed separately for the core region and boundary region. For each tumor, the entropy within the core is compared to that of the boundary, and the ratio can be the quantitative score associated with tumor severity. For example, tumors where the entropy value was similar between the core region and boundary region can be associated with a less severe tumor and thus better survival.

In some embodiments, the quantitative score for entropy is an indication of tumor density, wherein the method further comprises selecting adjuvant therapy for the subject if the quantitative score for entropy indicates a high tumor density.

Convexity

In some embodiments, the image feature is convexity. Convexity was developed to represent the semantic feature of "speculation", wherein multiple finger-like projections into the parenchyma are generally considered to be an indicator of a poor prognosis. In some embodiments, the convexity can be calculated by an algorithm that performs steps comprising: identifying a border of the segmented image; creating a mask of the segmented image; calculating the area of the mask of the segmented image; creating a convex hull of the border of the segmented image; calculating the area of the convex hull; and comparing the area of the mask to the area of the convex hull to calculate convexity.

As convexity can be calculated as the ratio between the area of the tumor mask and the area of the convex hull encapsulating the tumor, a convexity score of one corresponds to a circular or oval shape without concavities along its perimeter, while values smaller than one measure the deviation from any of these shapes (and hence, the severity of spiculations). A lower convexity score is reflective of a more irregular shape, which can be associated with a higher tumor severity and expected worse survival. Higher convexity scores described convex shapes with fewer spiculations and irregularities along the boundary, and can be associated with a lower tumor severity and better survival.

In some embodiments, the algorithm for convexity further comprises correcting for overlap with another structure, such as for example a NSCLC adenocarcinoma overlapping with the pleural wall. In some embodiments, the correction comprises: identifying a border of a structure; comparing the border of the structure with the border of the sample area to determine overlap between the sample area and the structure; and eliminating overlapping regions from the area of the mask of the sample area and the area of the convex hull used to calculate convexity.

Figure 19:
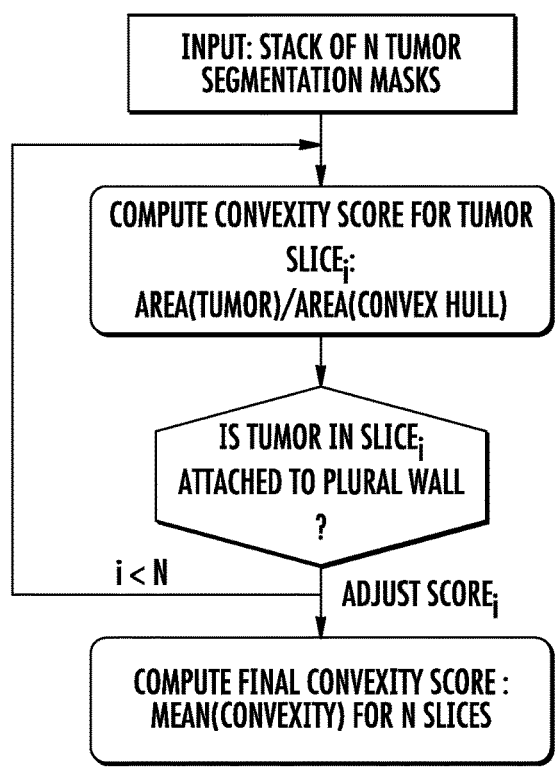
FIG. 19 is a schematic of an exemplary algorithm used to compute convexity.

In some embodiments, the quantitative score for convexity is calculated as the average of the convexity for each two-dimensional image slice in a three-dimensional stack. In some embodiments, the algorithm for convexity further comprises eliminating from the two-dimensional slices used to compute the average convexity score any two-dimensional slice that overlaps with the structure. This algorithm is further illustrated in FIG. 19.

In some embodiments, the quantitative score for convexity is an indication of either an irregular or convex tumor shape, wherein the method comprises selecting adjuvant therapy for the subject if the quantitative score for convexity indicates an irregular tumor shape.

Tumors

Any type of oncological disorder that produces a solid tumor can be evaluated via the methods discussed herein. Examples include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, and brain. Specific cancers contemplated for treatment include non-small cell lung cancer, such as lung adenocarcinomas.

Other examples of cancers that can be treated according to the methods disclosed herein are adrenocortical carcinoma, cerebellar astrocytoma, basal cell carcinoma, bile duct cancer, bladder cancer, bone cancer, brain tumor, breast cancer, carcinoid tumor, cervical cancer, colon cancer, endometrial cancer, ependymoma, esophageal cancer, gallbladder cancer, gastric (stomach) cancer, gastrointestinal carcinoid tumor, germ cell tumor, glioma, head and neck cancer, hepatocellular (liver) cancer, hypopharyngeal cancer, hypothalamic and visual pathway glioma, intraocular melanoma, retinoblastoma, islet cell carcinoma (endocrine pancreas), laryngeal cancer, lip and oral cavity cancer, liver cancer, medulloblastoma, Merkel cell carcinoma, squamous neck cancer with occult mycosis fungoides, myelodysplastic syndromes, nasal cavity and paranasal sinus cancer, nasopharyngeal cancer, neuroblastoma, oral cancer, oropharyngeal cancer, osteosarcoma, ovarian cancer, pancreatic cancer, paranasal sinus and nasal cavity cancer, parathyroid cancer, penile cancer, pheochromocytoma, pineoblastoma and supratentorial primitive neuroectodermal tumor, pituitary tumor, pleuropulmonary blastoma, prostate cancer, rectal cancer, renal cell (kidney) cancer, retinoblastoma, rhabdomyosarcoma, salivary gland cancer, Ewing's sarcoma, soft tissue sarcoma, Sezary syndrome, skin cancer, small cell lung cancer, small intestine cancer, supratentorial primitive neuroectodermal tumors, testicular cancer, thymic carcinoma, thymoma, thyroid cancer, transitional cell cancer of the renal pelvis and ureter, trophoblastic tumor, urethral cancer, uterine cancer, vaginal cancer, vulvar cancer, Waldenstrom's macroglobulinemia, and Wilms' tumor.

In some embodiments, the tumor comprises non-small cell lung cancer. In some embodiments, the tumor comprises lung adenocarcinoma.

Selecting Surgical or Adjuvant Therapy

The disclosed methods can further comprise selecting a course of therapy for the subject based on the quantitative score for the one or more image features. In some embodiments, the quantitative score for entropy is an indication of tumor density, wherein the method further comprises selecting adjuvant therapy for the subject if the quantitative score for entropy indicates a high tumor density. In some embodiments, the quantitative score for convexity is an indication of either an irregular or convex tumor shape, wherein the method comprises selecting adjuvant therapy for the subject if the quantitative score for convexity indicates an irregular tumor shape.

For example, the entropy and convexity image features disclosed herein were able to identify a subpopulation of stage I non-small cell lung cancer (NSCLC) adenocarcinoma patients, 30%-50% of those tested, as those with worse survival than expected by TNM staging alone. This is roughly the same percentage of the stage I NSCLC patients that do not survive 5 years post diagnosis despite successful surgery. This suggests that the entropy and convexity image features disclosed herein are able to select Stage I patients which may benefit from a more aggressive treatment course, such as adding adjuvant chemotherapy post-surgery.

Systems and Computing Devices

Also disclosed is a computer system comprising memory on which is stored instructions to perform the disclosed methods. For example, the memory can contain instructions to receive anatomical images acquired from a region of interest in a subject containing a tumor, segment the anatomical image to define a volume of interest representing the tumor, extract one or more image features from the segmented image, and generate a quantitative score for the one or more image features. In some embodiments, the image features are selected from the group consisting of entropy, convexity, or a combination thereof. In some embodiments, the quantitative score for the one or more image features can be associated with tumor severity.

Figure 18:
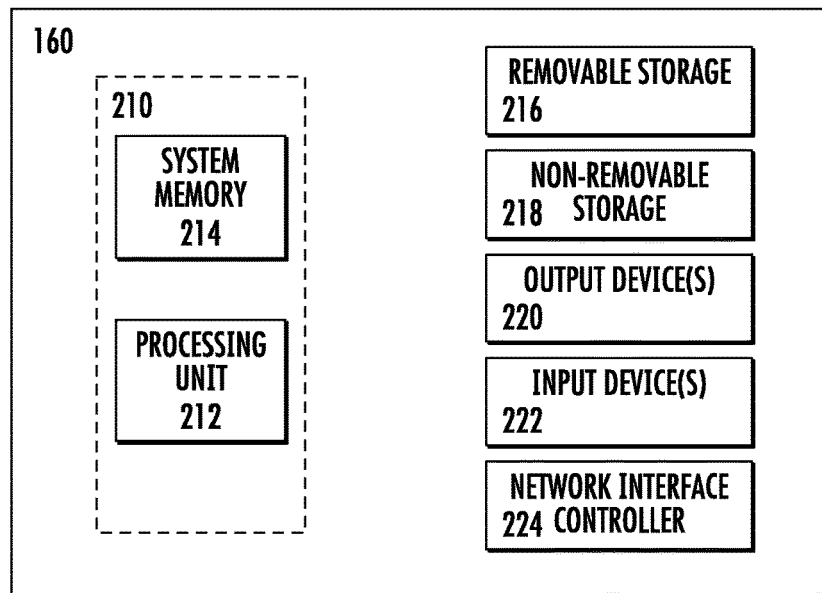
FIG. 18 is a schematic of an exemplary computing device.

FIG. 18 illustrates an example computing device upon which examples disclosed herein may be implemented. The computing device (160) can include a bus or other communication mechanism for communicating information among various components of the computing device (160). In its most basic configuration, computing device (160) typically includes at least one processing unit (212) (a processor) and system memory (214). Depending on the exact configuration and type of computing device, system memory (214) may be volatile (such as random access memory (RAM)), non-volatile (such as read-only memory (ROM), flash memory, etc.), or some combination of the two. This most basic configuration is illustrated in FIG. 18 by a dashed line (210). The processing unit (212) may be a standard programmable processor that performs arithmetic and logic operations necessary for operation of the computing device (160).

The computing device (160) can have additional features/functionality. For example, computing device (160) may include additional storage such as removable storage (216) and non-removable storage (218) including, but not limited to, magnetic or optical disks or tapes. The computing device (160) can also contain network connection(s) (224) that allow the device to communicate with other devices. The computing device (160) can also have input device(s) (222) such as a keyboard, mouse, touch screen, antenna or other systems configured to communicate with the camera in the system described above, etc. Output device(s) (220) such as a display, speakers, printer, etc. may also be included. The additional devices can be connected to the bus in order to facilitate communication of data among the components of the computing device (160).

The processing unit (212) can be configured to execute program code encoded in tangible, computer-readable media. Computer-readable media refers to any media that is capable of providing data that causes the computing device (160) (i.e., a machine) to operate in a particular fashion. Various computer-readable media can be utilized to provide instructions to the processing unit (212) for execution. Common forms of computer-readable media include, for example, magnetic media, optical media, physical media, memory chips or cartridges, a carrier wave, or any other medium from which a computer can read. Example computer-readable media can include, but is not limited to, volatile media, non-volatile media and transmission media. Volatile and non-volatile media can be implemented in any method or technology for storage of information such as computer readable instructions, data structures, program modules or other data and common forms are discussed in detail below. Transmission media can include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit (212) can execute program code stored in the system memory (214). For example, the bus can carry data to the system memory (214), from which the processing unit (212) receives and executes instructions. The data received by the system memory (214) can optionally be stored on the removable storage (216) or the non-removable storage (218) before or after execution by the processing unit (212).

The computing device (160) typically includes a variety of computer-readable media. Computer-readable media can be any available media that can be accessed by device (160) and includes both volatile and non-volatile media, removable and non-removable media. Computer storage media include volatile and non-volatile, and removable and non-removable media implemented in any method or technology for storage of information such as computer readable instructions, data structures, program modules or other data. System memory (214), removable storage (216), and non-removable storage (218) are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device (160). Any such computer storage media can be part of computing device (160).

It should be understood that the various techniques described herein can be implemented in connection with hardware or software or, where appropriate, with a combination thereof. Thus, the methods, systems, and associated signal processing of the presently disclosed subject matter, or certain aspects or portions thereof, can take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs can implement or utilize the processes described in connection with the presently disclosed subject matter, e.g., through the use of an application programming interface (API), reusable controls, or the like. Such programs can be implemented in a high level procedural or object-oriented programming language to communicate with a computer system. However, the program(s) can be implemented in assembly or machine language, if desired. In any case, the language can be a compiled or interpreted language and it may be combined with hardware implementations.

In certain examples, system memory (214) comprises computer-executable instructions stored thereon that, when executed by the processor (212), provide for analysis of anatomical images to obtain information about the tumor severity. To implement analysis of this type, the system memory (214) can comprise computer-executable instructions stored thereon that, when executed by the processor (212), cause the processor to: receive a anatomical images acquired from a region of interest in a subject containing a tumor; segment the anatomical image to define a volume of interest representing the tumor; extract one or more image features from the segmented image, wherein the image features are selected from the group consisting of convexity, entropy, or a combination thereof; and generate a quantitative score for the one or more image features, wherein the quantitative score for the one or more image features are associated with tumor severity.

The analysis of the anatomical images can be carried out in whole or in part on one or more computing device. For example, the system may comprise one or more additional computing device.

In certain examples, system memory (214) comprises computer-executable instructions stored thereon that, when executed by the processor (212), provide for analysis of the anatomical images to obtain image features, such as entropy, convexity or combinations thereof.

In some embodiments, the image feature is entropy. In some embodiments, the quantitative score is a ratio of the average entropy in a core region of the segmented image and the average entropy in a boundary region of the segmented image. In some embodiments, the ratio is calculated by an algorithm that performs the steps comprising: subdividing the segmented image into the core region and the boundary region; calculating an entropy coefficient for each pixel in the core region and the boundary region' averaging the entropy coefficients for the core region and the boundary region; and comparing the average entropy coefficient of the core region to the average entropy of the boundary region to obtain the entropy ratio. This algorithm is further illustrated in FIG. 20.

In some embodiments, the image feature is convexity. In some embodiments, the convexity can be calculated by an algorithm that performs steps comprising: identifying a border of the segmented image; creating a mask of the segmented image; calculating the area of the mask of the segmented image; creating a convex hull of the border of the segmented image; calculating the area of the convex hull; and comparing the area of the mask to the area of the convex hull to calculate convexity.

In some embodiments, the algorithm for convexity further comprises correcting for overlap with another structure, such as for example a NSCLC adenocarcinoma overlapping with the pleural wall. In some embodiments, the correction comprises: identifying a border of a structure; comparing the border of the structure with the border of the sample area to determine overlap between the sample area and the structure; and eliminating overlapping regions from the area of the mask of the sample area and the area of the convex hull used to calculate convexity.

In some embodiments, the quantitative score for convexity is calculated as the average of the convexity for each two-dimensional image slice in a three-dimensional stack. In some embodiments, the algorithm for convexity further comprises eliminating from the two-dimensional slices used to compute the average convexity score any two-dimensional slice that overlaps with the structure. This algorithm is further illustrated in FIG. 19.

Definitions

The term "individual," "host," "subject," and "patient" are used interchangeably to refer to any individual who is the target of administration or treatment. The subject can be a vertebrate, for example, a mammal. Thus, the subject can be a human or veterinary patient.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Computer Tomography (CT) has remained an important diagnostic tool and continues to be used for initial tumor staging. Diagnostic CT scans are routinely taken and interpreted by the radiologists as they can contain important prognostic and diagnostic information regarding the tumors. Quantifying these observations using computer analysis could provide systematic prognostic information not biased by the variability stemming from the radiologists expertise and workload. Due to the increasing number of therapy options for NSCLC patients, these prognostic biomarkers based on the patients' scans have the potential of individualizing and improving patient care.

The development of imaging features that can quantitative predict the severity of a tumor in a subject using retrospectively collected diagnostic CT images is described. The imaging features introduced herein follow and quantify the observations made by the experts reading diagnostic scans and can be robust, independent predictors of survival for patients with lung adenocarcinoma.

Currently, the choice of systematic treatment is predicated upon the stage and histological type of cancer. Additional variables, e.g. expression biomarkers such as epidermal growth factor receptor (EGFR) mutations, can be incorporated into the decision making process. However, NSCLC tumors are highly heterogeneous and thus the biomarker expressions might vary within the niches of the same tumor. This profound spatial heterogeneity echoes across different biological levels involving genes, cells, and tissues and is almost impossible to capture and quantify with biopsy based methods alone.

CT imaging, on the other hand, offers an overview of the tumor and can be used to assess the tumor region globally, as a function of intra- and intertumoral variability. Changes on the molecular level over time can become observable as related imaging phenomena; therefore, routinely obtained patient scans can contain potential biomarkers for prognostic decision making.

There has been an increase in research activity in the areas of lung nodule detection and classification using image processing and data mining algorithms but very little progress has been made in the development of prognostic imaging features for NSCLC patients. To date, few investigators have pursued the research of prognostic imaging features and the relationships between imaging features and disease course and biology in NSCLC.

CT imaging has remained an integral part of diagnosis and treatment planning of NSCLC tumors. Using diagnostic imaging, these tumors can be characterized based on their shape and margin morphology, density, and extent of internal enhancement and necrosis. The radiologists assessing the tumors rely on prior knowledge and are able to deduce the information based on visual cues. The human eye is remarkable at fusing information and detecting patterns while maintaining the awareness about the spatial distribution of the image cues in the scene. An expert reading the scan is capable of interpreting the information it contains using a continuous spectrum, which is often the result of prior knowledge and exposure to a variety of patient cases and their outcomes. This allows the radiologists to compare and differentiate between different degrees of 'bad' or 'good' prognostic markers, beyond the binary descriptors such as the mere presence or absence of a particular biological phenomenon.

However, the terminology used in radiology to characterize the pathological findings is subjective. Even with the introduction of a classification protocol and lexicon, such as Breast Imaging Reporting and Data Systems (BI-RADS) used in breast imaging reporting, studies have reported high interobserver variability in lesion interpretation among radiologists. Hence, in order to enhance clinical decision-making, it is essential to develop robust prognostic quantitative descriptors that are capable of capturing the information contained in individual patients' scans in a systematic and efficient fashion. As part of the initial investigation, the participating radiologists were asked to independently review the diagnostic scans for the NSCLC cohort and relay the key tumor descriptors.

One of the key aspects described by the radiologists when looking at the CT scans was density, or solidity, of the tumor. The radiologists working with the scans differentiated between nonsolid, partly solid and solid tumors. This range in tumor solidity was deemed prognostic, with solid tumors being described by the radiologists as more malignant and associated with a worse outcome.

When examining the diagnostic CT scans, the radiologists were able to describe the solidity of the tumor despite the differences in imaging parameters such as different X-ray kvp and reconstruction filters used. When reading the scan, they were able to abstract away the variability introduced by inconsistencies in image acquisition and reconstruction techniques, and instead focusing on the change of texture across the tumor as well as the contrast between the tumor and the surrounding tissues.

The radiologists were also asked to evaluate and compare scans reconstructed using different filters—when specifically asked to detect the differences, the radiologist could point out that one image appeared as a 'smoother version' of another, but that did not significantly hinder the reading of the scan. Yet, this difference in the image reconstruction technique, when not accounted for, can compromise reproducibility of the method and trigger differences in results if a naïve algorithm is used to quantify the feature across the entire region of interest. The shape of the lesion has an observed correlation with the tumor aggressiveness: slower growing, less aggressive tumors tend to grow out uniformly, thus forming round, convex shapes with well-defined, continuous borders. Aggressive cancerous tumors, on the contrary, tend to spread more quickly which contributes to irregular, concave shapes and spiculations, and ill-defined borders suggestive of proliferation.

Tumors are complex evolving systems that are continuously changing as a result of internal processes and the interaction with the surrounding environment. The microenvironment plays a role in tumor progression and response to therapy. The changes on the molecular level eventually extend to a more observable level and manifest themselves as, e.g., regions of necrosis, hemorrhage and vascularization that can be observable in CT images. At the same time, variables from the surrounding anatomy provide subtle cues and characteristics of tumor dynamics. Thus, the proliferative nature of the tumor and the growth rate can be deduced from examining the boundary of the tumor object. Likewise, location and availability of resources are important biomarkers and also require examining the interaction of the tumor region with its surrounding, as opposed to calculating features solely across the tumor region.

Hence, two distinct phenomena were pursued for imaging feature development: intratumoral changes within the region of interest (ROI) and the interaction of the tumor object with the surrounding environment. In order to quantify the intratumoral changes, the tumor region and the change in values across the core and edge sub-regions were examined. On the contrary, these internal changes in values are not of interest when the interaction between the tumor and the surrounding environment is being examined. Here, different levels of information are examined and changes in intensity and texture are abstracted away in favor of the overall shape of the tumor object.

When analyzing patient specific scans, the radiologists will often adjust the window-level contrast, in order to change the display contrast and brightness, thus enhancing particular phenomena they are trying to observe. The result of such an adjustment is purely visual, yet it allows the clinician to abstract away unimportant details while making relevant imaging features more prominent. To achieve a similar effect, a filter was applied to the entire ROI first and then the results of the filtering within the sub-regions of the tumor ROI were evaluated.

Materials and Methods

A retrospective analysis of surgically treated NSCLC cohort was undertaken. All patients had undergone resection of histologically confirmed NSCLC with a corresponding diagnostic CT obtained within 60 days of the diagnosis.

In order to assess the convexity of the tumor, only segmentation masks were used, which corrected for inconsistencies in image data created by the differences of imaging acquisition and reconstruction parameters. Instead of using either the middle slice or the largest slice, or creating a 3D voxel model, convexity was instead computed for each slice and then the statistics were calculated across the individual values.

Survival time was defined as the time between the time of diagnosis and the time of death. Statistical analysis was performed using R. Kaplan-Meier survival analysis was used to evaluate the prognostic significance of the convexity feature. Two prognostic groups were formed by splitting the feature scores at the median value. The difference between two survival curves was evaluated by using a nonparametric log rank test. P values of <0.05 were considered statistically significant.

Results

Patient Cohort

A total of 235 patient CT scans were collected representing retrospective NSCLC. All clinical stages and NSCLC histological subtypes was considered for the initial data set. Table 1 shows the distribution of key clinical parameters in this study.

TABLE 1

Heterogeneity of clinical parameters in the NSCLC radiomics cohort.

| Histology | Total | Mean Age at Rx | Mean survival time (months) | Alive | Dead |
|---|---|---|---|---|---|
| Adenocarcinoma | 87 | 67 | 29 | 47 | 40 |
| BAC | 51 | 71 | 31 | 36 | 15 |
| Squamous cell | 63 | 70 | 33 | 37 | 26 |
| Other | 34 | 66 | 35 | 21 | 13 |

While these different histopathologic subtypes are combined in the NSCLC study cohort, they introduce additional variability based on their unique cell biology and prognostic signatures. Hence, in order to minimize the confounding effect of clinical parameters variability, the study was restricted to a single histological subtype. The prognostic imaging features were developed and tested on the adenocarcinomas as they constituted the largest subgroup of the original radiomics dataset.

Demographic and clinical variables such as gender, smoking status and TNM stage of the tumor are known to be independently prognostic factors. Studies have shown that the prognosis of lung cancer is different in men and women, and regardless of the key factors such as stage, histology and treatment protocol, women live longer. The frequency of genomic alterations has been shown to differ between sexes which can lead to differences in response treatment and prognosis between patients. As a result, the presence and the skewness of the distribution of these clinical variables introduce additional heterogeneity to the study dataset. For example (Table 1), the squamous cell carcinoma subset of patients had a larger representation of males, while the rest if the histological subgroups are dominated by female patients.

TNM stage alone is a highly statistically significant prognostic factor. Currently, the TNM staging system, along with performance status, remains the most validated survival predictor and it is used frequently for treatment decision making. While the dataset consists predominantly of early stage (I and II) cancers, their distribution within the histological subclasses varies (Table 1). Within the adenocarcinoma study cohort, the dataset was further refined to contain an even distribution of TNM stages I-III (n=62).

It is important to point out that this clinical heterogeneity is not unique to the study cohort herein, and it is instead reflective of the variability routinely present in complex retrospective studies. Although it is desirable to increase the size of the cohort in order to secure a signal to noise ratio large enough to observe a phenomenon of interest, the discoveries can be confounded by the presence of independent prognostic parameters, such as gender and smoking status, and their distribution variability. Likewise, further validation of the results might not be carried out in a similar cohort, since its inherent heterogeneity will make it different from the original discovery set.

Image Acquisition and Reconstruction Parameters Vary in Retrospectively Collected Data The radiomics study process involves a number of distinct steps such as image acquisition and reconstruction, segmentation and rendering, feature extraction, and the subsequent quantification and ad hoc informatics analyses of the features. Variability across sets of patient CTs exist even with when a standardized image acquisition protocol is established prior to the data collection. For example, variations in tube voltage across different CT systems and adjustments made based on the size of the patient will result in slightly different CT scans.

A retrospective image analysis study introduces additional variability to the differences in image acquisition and reconstruction. This in itself is an interesting challenge as differences in the CT reconstruction filters, as well as slice thickness and resolution, can directly influence the reproducibility of image feature values. Yet this variability is more reflective of the real clinical applications which often include a complex cohort of patient imaging data.

For the NSCLC cohort, different models of scanners were used, resulting in different 25 different convolution kernels, difference in X-ray tube voltages (ranging between 120-140 kVp), a range of pixel resolutions and reconstructed slice thicknesses spanning from 1 to 10 mm.

Convexity Describes Tumor Morphology and Irregularity of the Border Across the Slices Two imaging features were developed from diagnostic CT scans that capture the shape and texture changes within the tumor, using 2D stacks of CT scans. It was quantitatively demonstrated in 62 NSCLC CT studies that the developed imaging features are capable of classifying patients based on CT scans alone into two prognostic categories within statically significant bounds.

Figure 2:
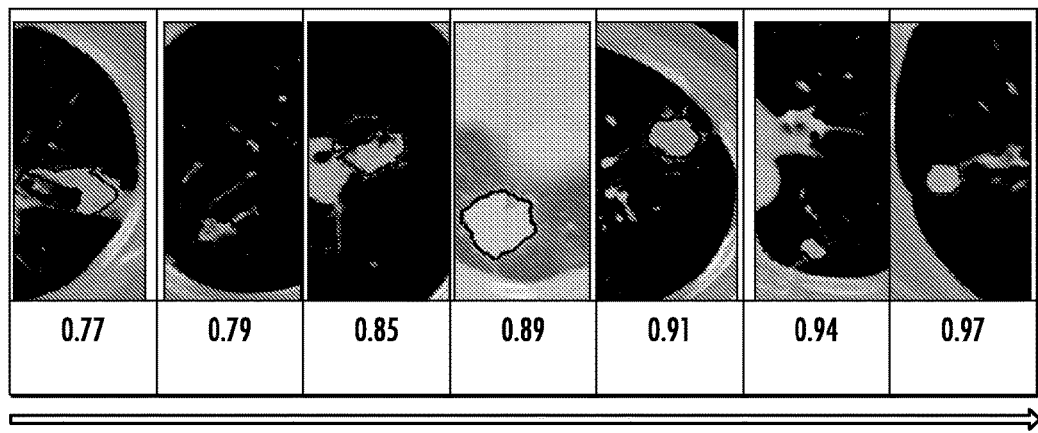
FIG. 2 depicts the range of values produced by the convexity feature that tracks the distribution of shapes present in the cohort, with the low values corresponding to more complex shapes and higher values corresponding to rounder and more well-defined lesions.
Figure 3:
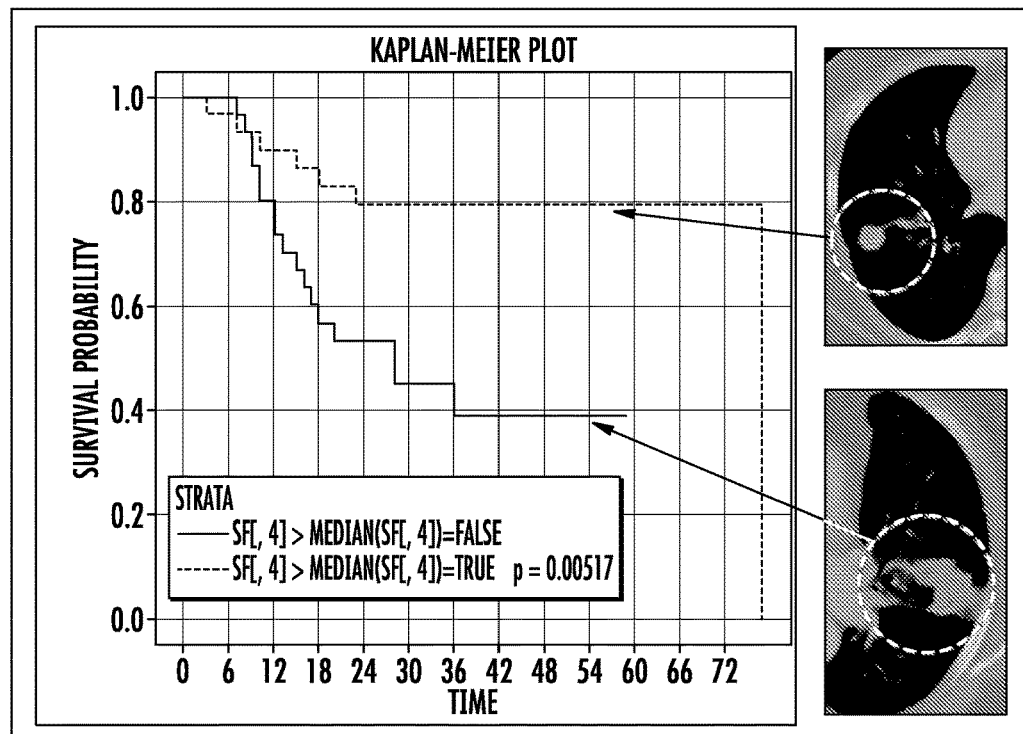
FIG. 3 depicts Kaplan-Meier estimates for the good and poor prognostic groups according to their convexity score.

Using the convexity imaging feature, it was possible to quantify the change in the tumor shape from round to more complex and irregular. FIG. 2 shows how the values of the imaging feature computed across the slices containing the tumor are capable of tracking the shapes, where lower convexity values represent irregular shapes and higher convexity values correspond to convex shapes. FIG. 3 shows the Kaplan-Meier estimates for the good and poor prognostic groups according to their convexity score.

Figure 4:
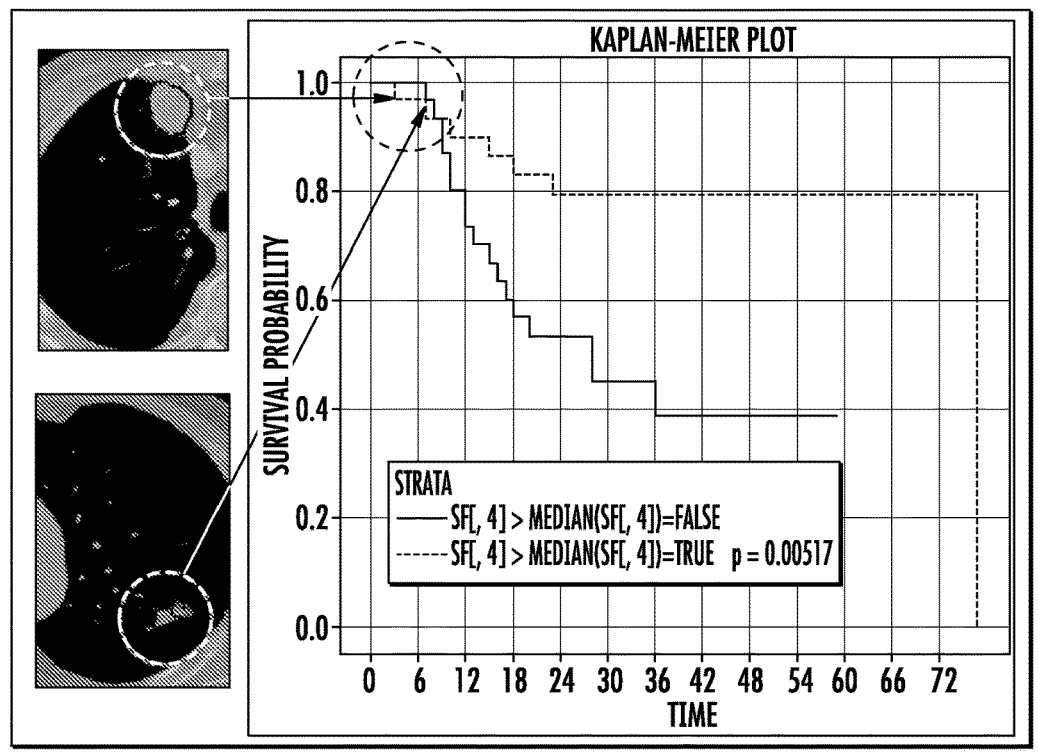
FIG. 4 depicts how the surrounding anatomy can compromise the convexity descriptor's capabilities.

Since tumors not only infiltrate but also compete with the surrounding anatomical structures, their intended shape can be compromised. Hence, despite the aggressiveness profile of the tumor, such structures as fissure lines or a pleural wall, can make the otherwise distorted and irregular tumor appear more round on the CT scan (FIG. 4).

Figure 5:
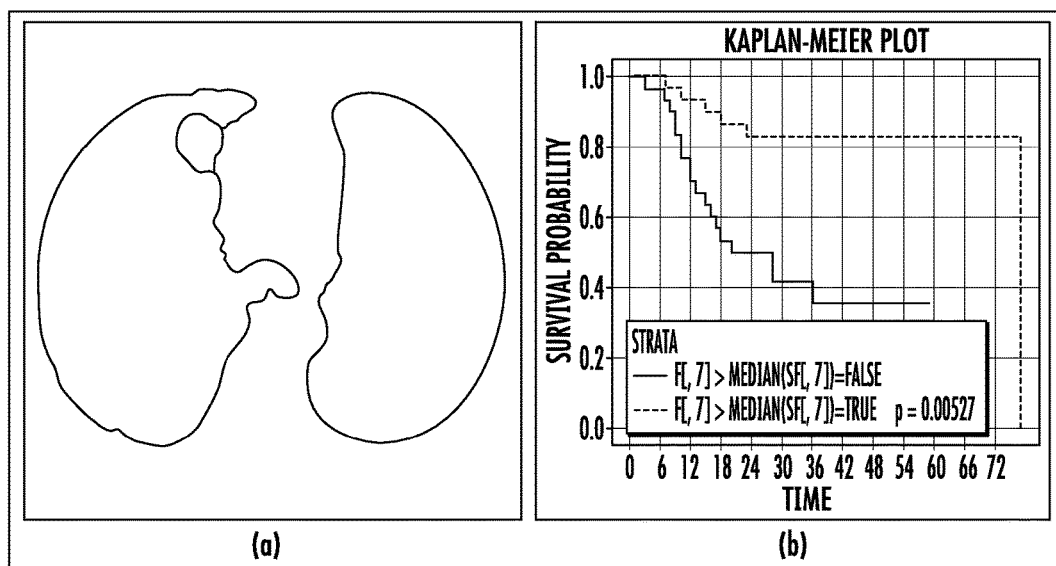
FIG. 5 depicts a tumor that is determined to be attached to the pleural wall, and how the average convexity value is weighted down using regions of the tumor that are not attached.

To correct for the shape distortion artifact caused by the pleural wall attachment, the algorithm was adjusted to automatically detect the cases in which a significant portion of the tumor's perimeter overlaps with the pleural wall. Since the cumulative convexity across all the slices containing the tumor was compute, it was possible to adjust the convexity score when it was determined that a significant percentage of the tumor perimeter was involved in the pleural wall attachment. The convexity values were recomputed for the adenocarcinoma cohort using pleural wall attachment correction. FIG. 5 shows that adjusting for tumor attachment improves the capability of the convexity biomarker to predict survival outcomes.

Figure 6:
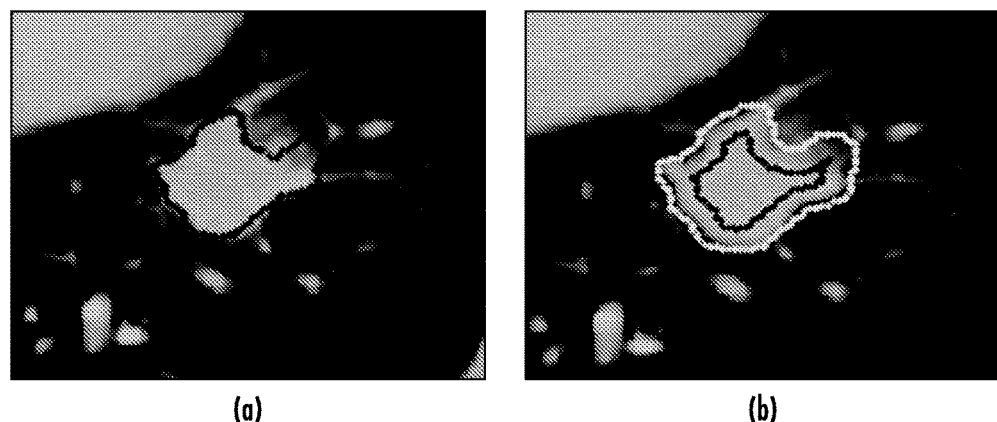
FIG. 6 depicts how imaging characteristics of the core and boundary sub-regions differ.

Contrast Between the Core and Border Regions of the Tumor Describes Tumor Solidity In order to adequately assess the intratumoral differences across the ROI, two filters were generated based on the originally semi-automatic segmentation of each tumor slice. Using the mask of the segmented ROI (FIG. 6a), the ROI was further subdivided into core and boundary subregions (FIG. 6b) using a series of morphological operations.

As the tumor expands and interacts with the surrounding environment, the intratumoral density differs across the ROI. At the tumor interface, there is an apparent edge effect which manifests itself in larger change in intensity values. The gradient in the edge region of the tumor tends to be higher than across the tumor, and as a result, can skew and average out the result of the evaluation carried out across the entire tumor region.

Figure 7:
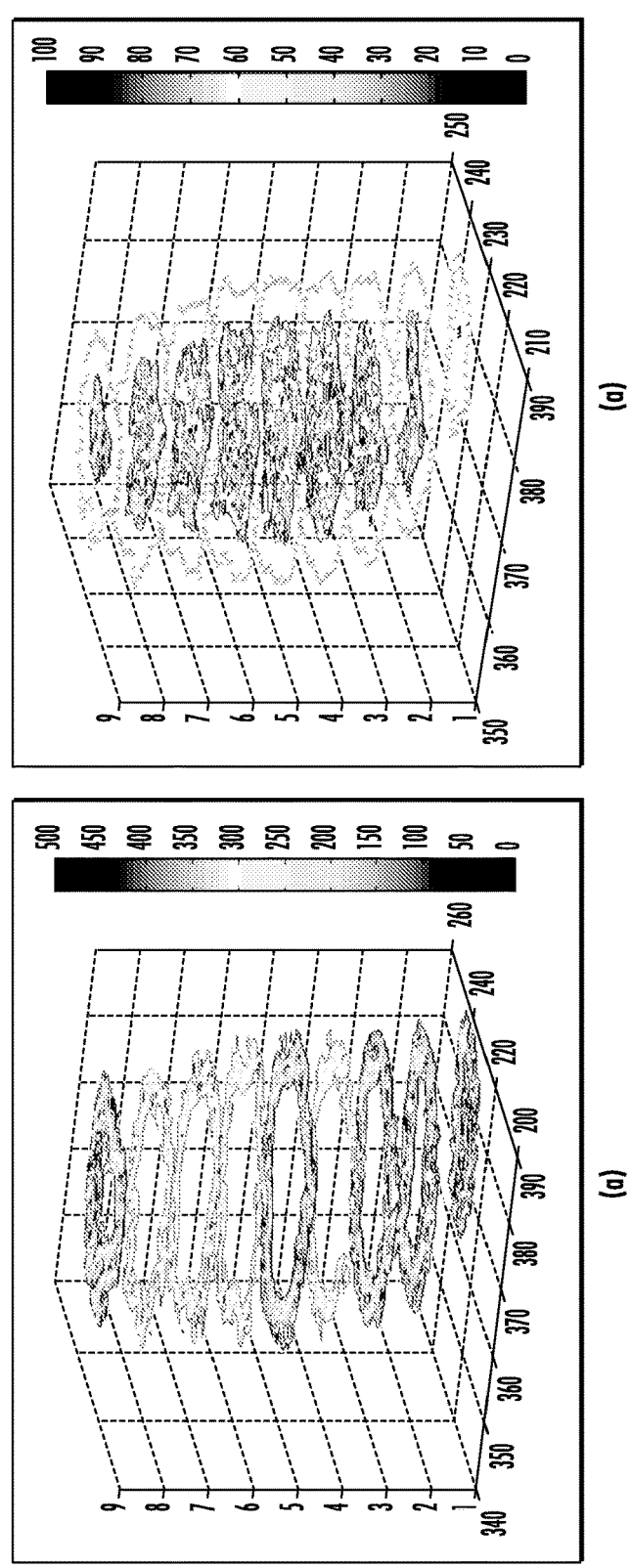
FIG. 7 depicts the difference in the gradient values between the core and the boundary regions.

As part of the experiment, the change in intensity values for each pixel was calculated over a surrounding [7×7] pixel window across the entire tumor region. The segmented tumor region was extended, in order to avoid introducing the edge effect of comparing against segmented out background, and then the values were cropped back to the original ROI. The resultant gradient magnitudes can be viewed as a 'terrain' where at each point in the image the height is determined by the magnitude of the gradient. The contour plot can be generated as a 2D projection of the 3D terrain (FIG. 7). When the contour plot was generated for the entire tumor region, the values along the edge were significantly higher, hence visually suppressing the contours in the center of the tumor region (FIG. 7a). The experiment was adjusted and the gradient maps were cropped to only include the core regions and the changes emerged, with a significantly smaller range of in gradient values. FIG. 7b shows the results of cropping the tumor region to core only, and dotted lines indicate where the original segmentation was before the cropping.

While the values along the edge of the tumor can compromise the evaluation of intratumoral imaging phenomena, they too contain important diagnostic and prognostic characteristics since they reflect on the interaction between the tumor and the surrounding tissues.

Figure 8:
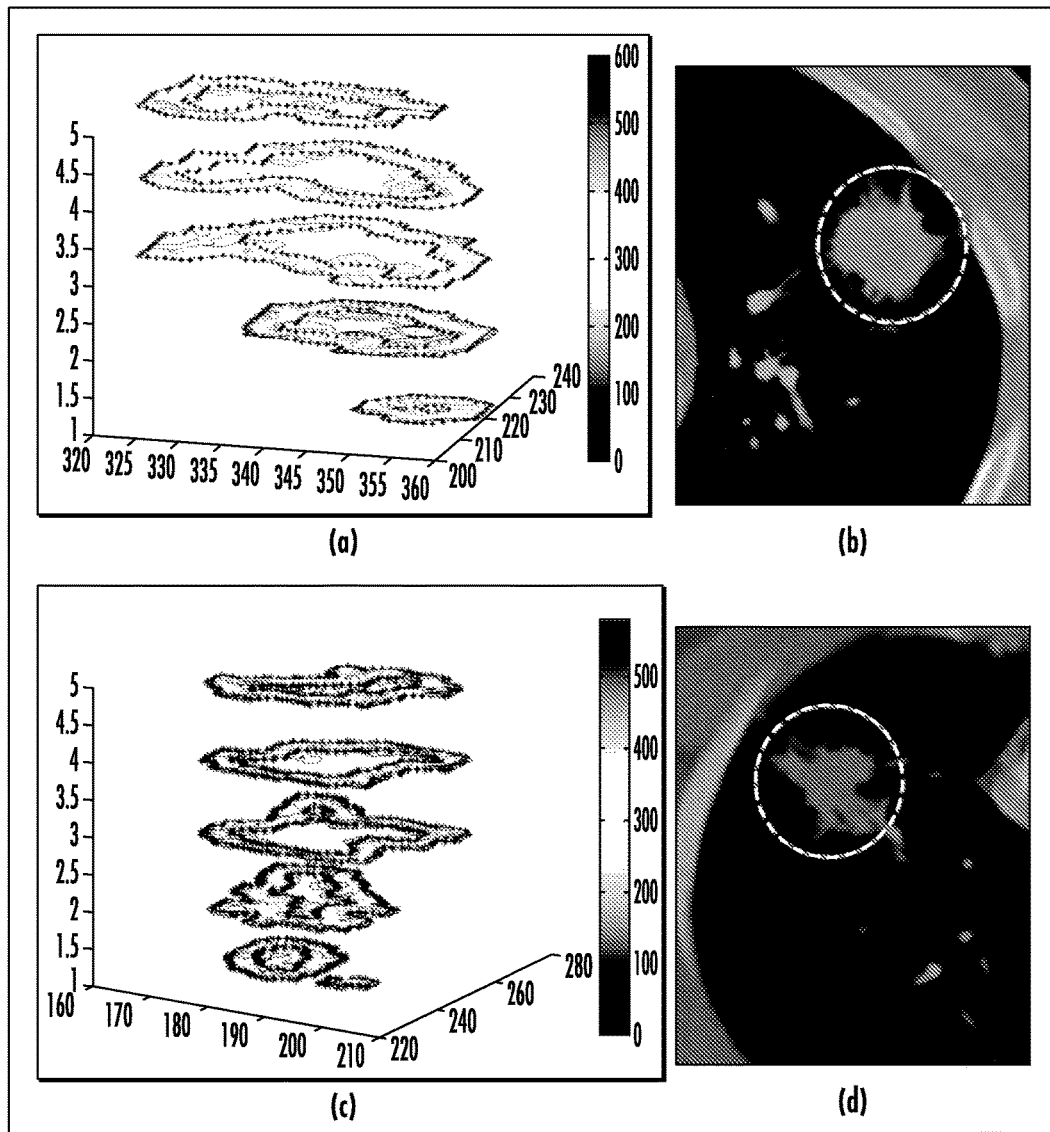
FIG. 8 depicts how in high density tumors relatively low values in the center of the region can cause the contour plots to manifest these as an empty core.

Interestingly, the contour plots for the regions of interests filtered using local entropy filter produced two classes of graphs. For some tumors, regardless of the size and the number of slices involved, there was a well-defined edge region which essentially drowned the entropy values across the core (FIG. 8). When compared with the original CT scans, the tumors had a more solid appearance.

Figure 9:
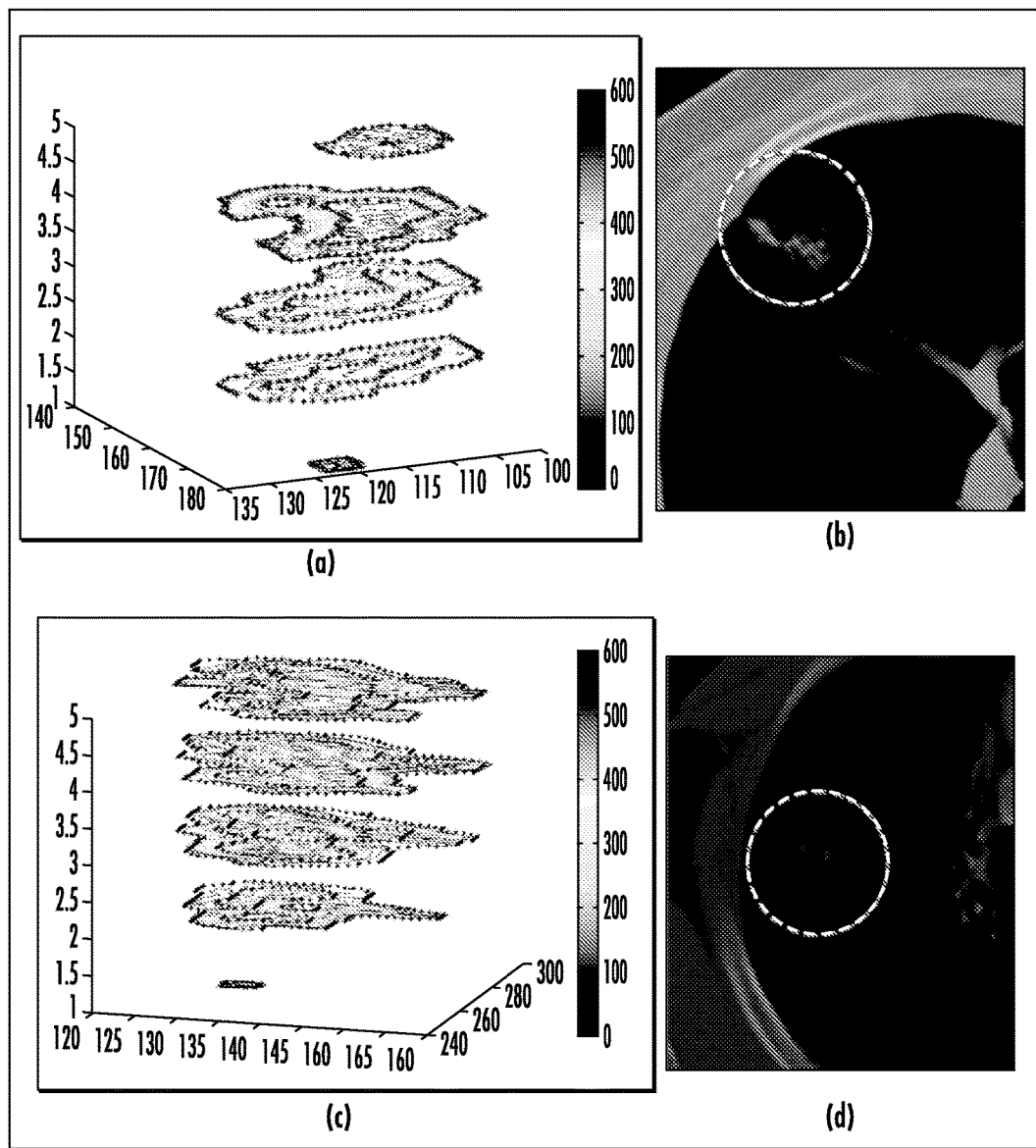
FIG. 9 depicts how low density tumors display a consistent gradient throughout the entire tumor region.

In the second group, the entropy values remained consistently the same across the entire tumor region, and the values in the edge region did not overpower the values in the core (FIG. 9). Hence, these graphs did not have a well pronounced core in the middle. When the scans from which these contour plots were generated were examined, the images revealed less dense tumors lacking a well-defined interface between them and the background anatomy.

As a result of the observation, not only were the statistics based on the entropy filtering across the entire tumor region for all the image slices containing the tumor computed, but records were also kept for the values in the predefined core and edge sub-regions. Since contrast between the two regions appeared important, instead of using just the statistics for the sub-regions and analyzing them independently of each other, contextual information was added by evaluating the differences between the core and edge regions.

Location-Specific Entropy-Based Markers are Prognostic in Lung Adenocarcinoma

Figure 10:
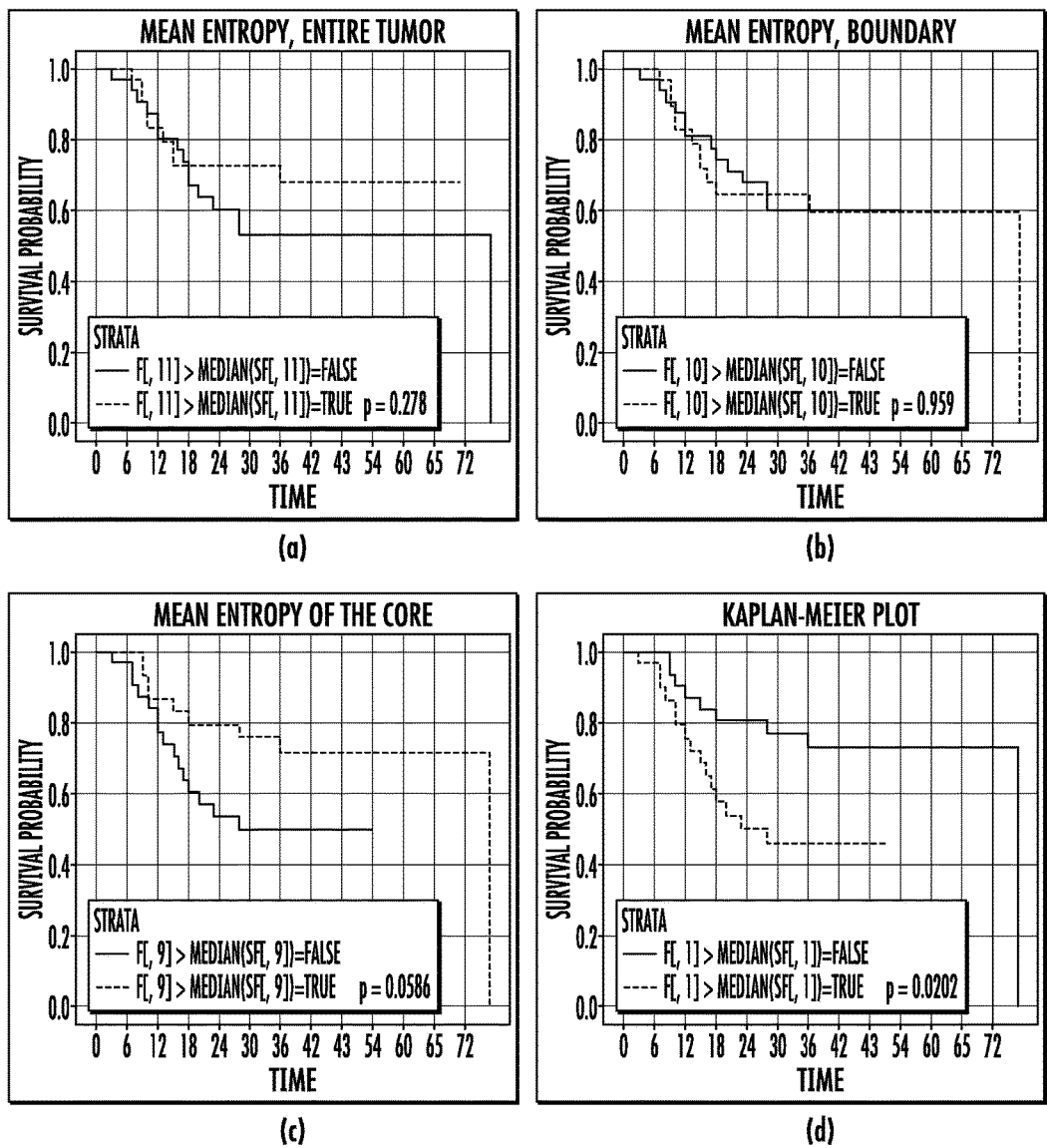
FIG. 10 depicts the mean entropy of (a) the entire region and (b) the boundary do not provide a good separation, with the boundary region influencing the values for the entire tumor region. Evaluating the contrast between (b) the boundary and (c) the core is, on the other hand, informative for (d) survival.

Using Kaplan-Meier survival analysis, the performance of the entropy imaging feature was evaluated. When entropy was computed for the entire segmented region, indiscriminately of either the core or boundary regions, the results were not statistically significant (FIG. 10a). Evaluating entropy along the boundary only was also not prognostically significant (FIG. 10b) and it appeared that the presence of entropy values along the edge skewed the results of the feature for the entire tumor. The entropy evaluated in the core region only (FIG. 10c) proved to be a great improvement. The filter for the entropy of the core enhanced such intratumoral characteristics as necrosis and spatial heterogeneity. Interestingly, even more improvement was achieved by contrasting the entropy values in the core and the edge sub-regions (FIG. 10d).

Figure 11:
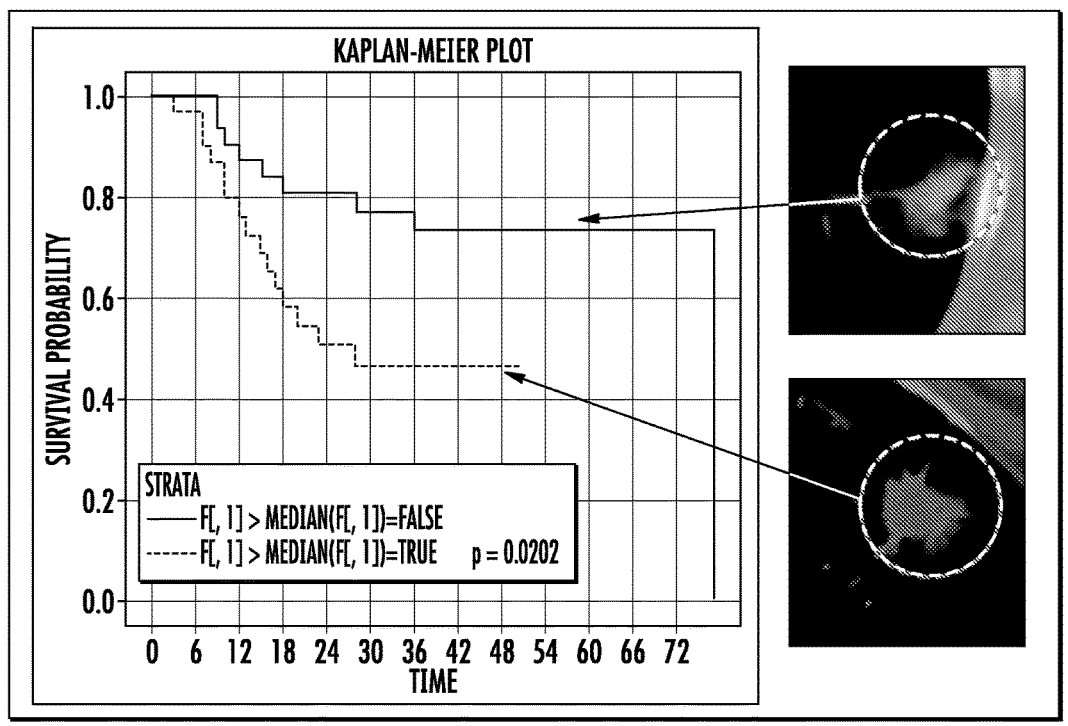
FIG. 11 depicts how CT scans representative of the two prognostic groups formed by the entropy based image feature appear differently.

The prognostic significance of the entropy based features was evaluated using a log-rank test and it was determined that contrasting the entropy values in the core and edge sub-regions was most predictive of survival outcomes. Then, the appearances of the tumors in the two prognostic groups based on the entropy value in the original CT scans were also compared. The tumors in the two prognostic groups looked different in the CT scans, as shown in FIG. 11. Tumors for which the entropy was consistent throughout the core and boundary regions have a better survival outcome. On the other hand, tumors where the contrast between the core and the edge regions was significant are associated with worse prognosis and appear dense or more solid in the scans. This observation also follows the analysis of the screens given by radiologists reading the scans and describing the tumor regions based on their 'solidity'.

The entropy feature is a statistical measure of randomness which is calculated based on the histogram counts within a sliding window. The spatial location of evaluating entropy was further restricted by using filters for core and boundary regions of the tumor. While the variability in image acquisition and reconstruction parameters has an effect on intensity based features, by evaluating the difference between the core and the boundary sub-regions, the feature is less sensitive to the inconsistencies in image formation.

Example 2

Materials and Methods
Study Population and Data

Imaging and clinical data were obtained on patients diagnosed with primary lung adenocarcinoma who were treated in the Thoracic Oncology Program at the H. Lee Moffitt Cancer Center and Research Institute; and the Maastricht Radiation Oncology Clinic (MAASTRO). The Moffitt cohort included 61 patients and the independent MAASTRO cohort included 47 patients. Inclusion criteria for Moffitt included patients who underwent surgical resection and had corresponding pre-surgery diagnostic CTs obtained within 60 days of the diagnosis. MAASTRO patients were referred for radiation therapy, and did not require surgical resection for inclusion.

Clinical data were obtained from Moffitt's cancer registry, which abstracts self-report information and clinical data from patient medical records including demographics, diagnosis, stage, and treatment. Follow-up for survival analyses occurs annually through passive and active methods. Patients seen for second opinions are not included in the Cancer Registry database because they do not fall under current reportable state and/or federal guidelines. Follow-up for vital status information occurs annually through passive and active methods. Pathologic TNM staging was utilized when available and clinical stage was used if these pathologic staging was missing. For this analysis smoking status was categorized as self-report ever smoker (current or former smoker) or never smoker.

Image Data Acquisition and Feature Extraction

All CT scans in this analysis had a slice thickness less than 6 mm. Patient CT scans were segmented to identify lung fields and tumors. The delineation of the lung fields was carried out using the Lung tumor analysis (LuTA) tool within the Definiens software platform. Cognition Network Technology was developed by Definiens AG and Merck & Co., Inc. After the lung field segmentation, an experienced radiologist identified the tumor in one of the CT slices. This was used as an initial seed-point for the single click ensemble 3-D segmentation algorithm (Gu, Y et al. *Pattern Recognit.* 2013, 46(3), 692-702). Performing semi-automatic segmentation not only decreased user interaction and eliminated the need for a manually drawn boundary, but also provided robust, reproducible and consistent delineation of the tumor region across the CT slices. It has previously been demonstrated that the single click ensemble segmentation algorithm reduced inter-observer variability while capturing the intricacies and important details of the tumor boundary (Gu, Y et al. *Pattern Recognit.* 2013, 46(3), 692-702). The tumor and lung were segmented for each of the patient image series.

Thus, for each patient, an original set of CT scans in DICOM (Digital Imaging and Communications in Medicine) format, the corresponding gray-scale intensity equivalents and binary masks for lung and tumor objects were collected. Image feature extraction and quantification for convexity and entropy was carried out in MATLAB.

Convexity Morphological Feature

Convexity was developed to represent the semantic feature of "spiculation", wherein multiple finger-like projections into the parenchyma are generally considered to be an indicator of a poor prognosis. Convexity was calculated as the ratio between the area of the tumor mask and the area of the convex hull of the tumor border. The convex hull was computed by defining the smallest convex polygon enclosing a planar ROI. A shape is convex if a line segment connecting any two points that are part of the shape is also part of the shape. Hence, the ratio between the area of the tumor mask and its convex hull described the amount of substantial protuberances and depressions along the tumor margin.

In order to minimize the effect of differing slice thickness, the calculation was performed individually on each slice and a mean score was calculated using all slices for the tumor. A convexity score of one corresponded to a shape that does not present with any concavities along its perimeter (e.g., sphere, box). Convexity scores less than one measure the degree of deviation from any of these shapes. Hence, this is a measure of severity of spiculations present in the tumor and concavities along its perimeter.

To account for smoothing artifacts caused by pleural wall interaction, a detection mechanism was incorporated for cases in which an overlap between the tumor boundary and the pleural wall exist. For each slice, tumor and lung field perimeters were extracted and compared. If an overlap in the perimeters is detected, the convexity algorithm automatically adjusted the convexity score for the entire volume of interest (VOI) by eliminating individual slices with the pleural wall overlap from the calculations.

Entropy

Entropy is one measure of attenuation heterogeneity in CT scans, which is also an indicator of a poor prognosis. An entropy filter was applied to the grayscale equivalent of the CT scan. The entropy filter is the implementation of Shannon entropy. In the image processing context, it is a texture-based statistical measure of the variation in the histogram distribution which reflects the predictability of intensity values within a given region of interest (ROI), and hence the underlying imaged tissue. For each pixel in the ROI, entropy was computed within the sliding [5×5] window surrounding it as $-\text{sum}(p_i * \log 2(p_i))$ where $p_i$ represents the frequency of the given intensity value, using a default histogram with 256 intensity bins.

To account for intratumoral differences and edge effects, the original ROI of the entire tumor was subdivided into two distinct regions—core and boundary—using a series of morphological operations. Each slice in the tumor VOI was extended using a dilation operation, to capture the full extent of the tumor edges and the interface between the tumor and the surrounding environment. The dilation was performed by convolving the original ROI with a structural element of a fixed size (3×3) sliding along its perimeter. When the tumor ROI was dilated, a check was performed to make sure the dilated region remained within the segmented lung region. Likewise, to exclude the edges from the core region, each ROI in the tumor volume was shrunk by removing pixels along the perimeter using an erosion operator. To ensure that enough pixels would remain for texture analysis within the core region, the size of the eroding element varied between 3×3 and 5×5 pixels. Difference between the dilated and eroded ROI masks produced a boundary mask.

The subdivision of the original ROI into the core and boundary was driven by the hypothesis that these regions reflect unique, spatially explicit biological processes, e.g. necrosis in the core and proliferation along the boundary.

Since entropy values were computed for each pixel in all slices, a 3-dimensional matrix of entropy coefficients was generated. Masks for the original tumor segmentations as well as the core and boundary masks were used to extract entropy values specific to those regions. Based on these values, volume of interest (VOI) specific cumulative statistics such as mean of entropy coefficients without the boundary, core and tumor VOIs were computed.

Statistical Analyses

The imaging feature data, demographic information, and vital status data were merged into a single file for subsequent statistical analyses using Stata/MP 12.1 (StataCorp LP, College Station, Tex.). Student's t-test and ANOVA were used to test for differences in imaging features by the demographic features and imaging parameters. A correlation matrix was used to assess correlation between the imaging features. Survival analyses were performed using Cox proportional hazard regression, Kaplan-Meier survival curves, and the log-rank test. The imaging features were dichotomized into two groups using the median score value.

Results

Patient Cohort and Image Acquisition Parameter Variability

A retrospective image analysis study faces variability in image acquisition and reconstruction inherent to routine clinical practice. Differences in CT reconstruction filters, as well as slice thickness and resolution, can inadvertently affect the reproducibility of imaging feature values. Moreover, differences in clinical characteristics can impact on the final analysis. Table 2 shows some of the clinical and imaging characteristics for this cohort of 61 patients with lung adenocarcinoma. CT scans collected from this cohort varied in terms of a number of key image acquisition and reconstruction parameters. X-ray tube voltages ranged between 120 and 140 kVp, slice thickness varied from 2.5 mm to 6 mm and pixel resolution ranged from 0.58 mm to 0.95 mm. All CT scans were contrast enhanced. This variability is representative of clinical applications that include patient imaging captured during the course of clinical care rather than for research purposes.

TABLE 2

Distribution of study population demographics and imaging parameters by imaging biomarkers

| | | | Imaging Features | | | | |
| | | | Entropy ratio | | Tumor volume | | Convexity | |
| Characteristic [1] | No. | (%) | Mean | (SD) | Mean | (SD) | Mean | (SD) |
|---|---|---|---|---|---|---|---|---|
| Overall | 61 | (100.0) | 1.41 | (0.26) | 7884.6 | (11205.9) | 0.87 | (0.07) |
| Demographics | | | | | | | | |
| Age at diagnosis | | | | | | | | |
| <65 | 20 | (32.8) | 1.42 | (0.05) | 11436.4 | (−3651.2) | 0.87 | (0.02) |
| ≥65 | 41 | (67.2) | 1.4 | (0.04) | 6152 | (1129.7) | 0.86 | (0.01) |
| P-value | | | 0.834 | | 0.084 | | 0.829 | |
| Gender | | | | | | | | |
| Female | 30 | (49.2) | 1.35 | (0.04) | 6467.9 | (1462.0) | 0.87 | (0.1) |
| Male | 31 | (50.8) | 1.46 | (0.05) | 9255.6 | (2444.3) | 0.87 | (0.1) |
| P-value | | | 0.102 | | 0.336 | | 0.995 | |
| Stage | | | | | | | | |
| Stage I | 25 | (41.0) | 1.36 | (0.27) | 5875.2 | (10830.4) | 0.87 | (0.07) |
| Stage II | 19 | (31.2) | 1.44 | (0.24) | 9791.5 | (10927.1) | 0.86 | (0.09) |
| Stages III and IV | 17 | (27.8) | 1.42 | (0.25) | 8708.2 | (12217.9) | 0.87 | (0.07) |
| P-value | | | 0.59 | | 0.493 | | 0.817 | |
| Imaging Parameters | | | | | | | | |
| Voltage, KvP | | | | | | | | |
| 120 | 57 | (93.4) | 1.42 | (0.26) | 8187.2 | (11510.8) | 0.87 | (0.08) |
| 130 or 140 | 4 | (6.6) | 1.22 | (0.19) | 3572.3 | (3406.5) | 0.85 | (0.03) |
| P-value | | | 0.124 | | 0.431 | | 0.761 | |
| Convolution kernel | | | | | | | | |
| B30F | 8 | (13.1) | 1.47 | (0.24) | 3314.3 | (4500.1) | 0.845 | (0.13) |
| B40f | 19 | (31.2) | 1.31 | (0.15) | 11752.4 | 1(5712.3) | 0.837 | (0.07) |
| B41F | 22 | (36.1) | 1.46 | (0.25) | 6487.3 | (7959.1) | 0.889 | (0.05) |
| Other [3] | 12 | (19.7) | 1.44 | 0.37) | 7369 | (10095.2) | 0.884 | (0.08) |
| P-value | | | 0.222 | | 0.269 | | 0.101 | |
| Slice thickness, mm | | | | | | | | |
| <5.0 | 18 | (29.5) | 1.47 | (0.26) | 9836.8 | | 0.844 | (0.1) |
| ≥5.0 | 43 | (70.5) | 1.38 | (0.25) | 7067.4 | (11301.7) | 0.875 | (0.06) |
| P-value | | | 0.181 | | 0.383 | | 0.142 | |
| Pixel resolution[4], mm | | | | | | | | |
| <0.6926 | 20 | (32.8) | 1.44 | (0.25) | 8013.6 | (10733.4) | 0.875 | (0.06) |
| ≥0.6926 to <0.7785 | 20 | (32.8) | 1.36 | (0.21) | 10414.8 | (14356.6) | 0.878 | (0.09) |
| ≥0.7785 | 21 | (34.4) | 1.49 | (0.29) | 5352.1 | (7636.5) | 0.845 | (0.09) |
| P-value | | | 0.529 | | 0.357 | | 0.29 | |

Figure 12A:
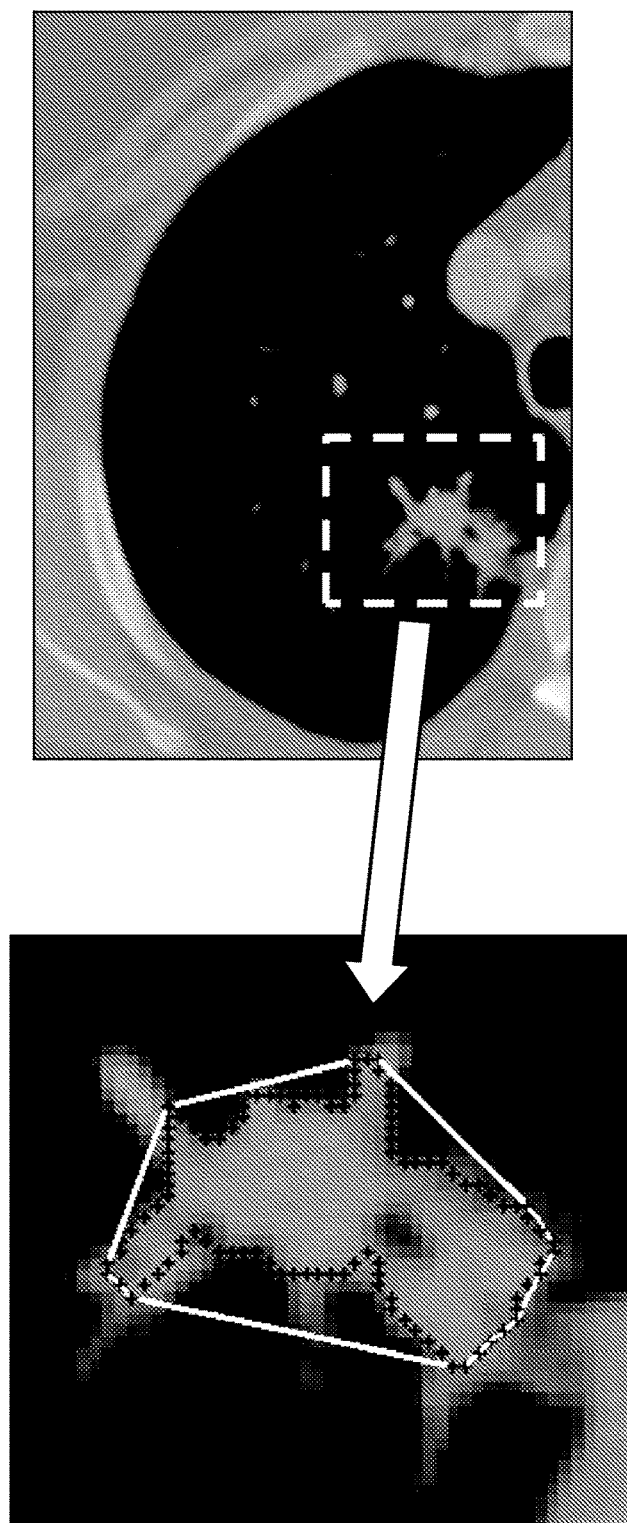
FIG. 12a depicts how the convexity feature measures the shape of the tumor as a ratio of tumor border to convex hull.
Figure 12B:
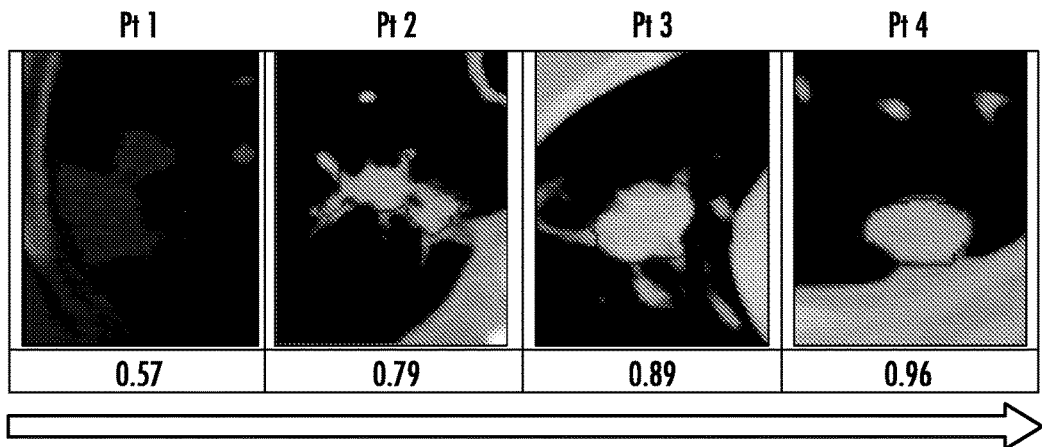
FIG. 12b depicts that the convexity feature tracks the change in tumor morphology.
Figure 12C:
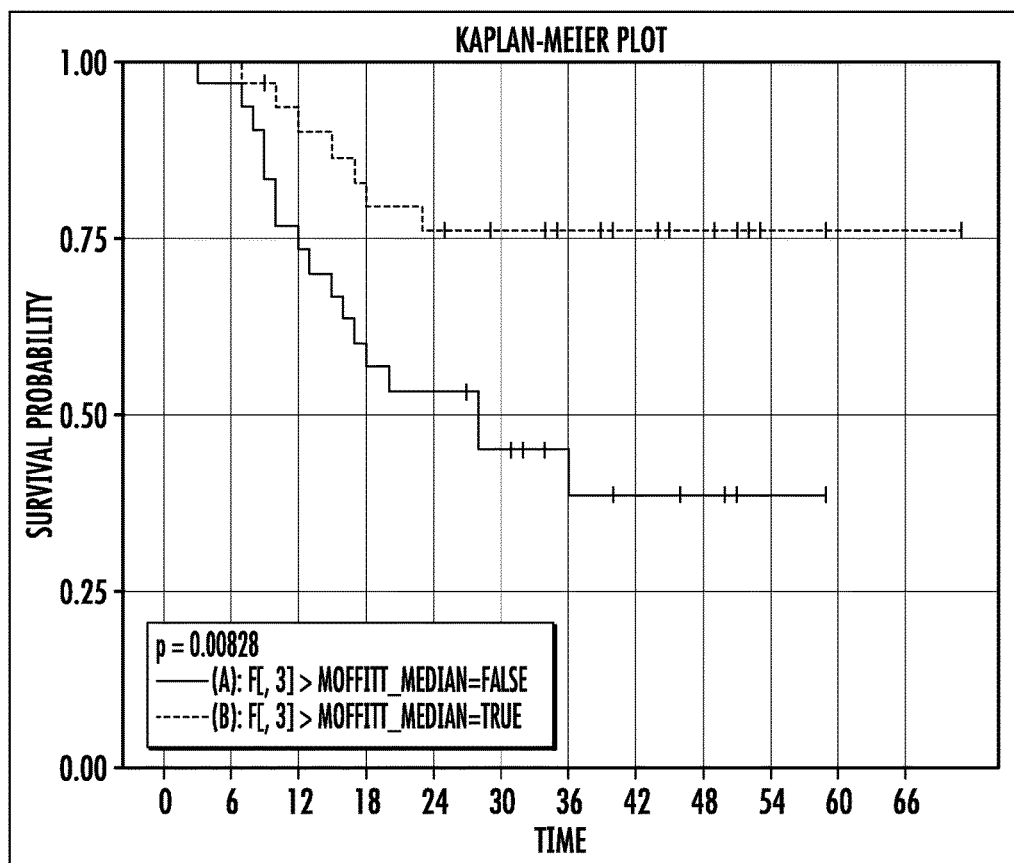
FIG. 12c depicts that convexity is predictive of patient overall survival when dichotomized at the median value.

[1] 96.7% (No. = 59) of this study population were ever smokers and 96.7% (No. = 59) were White race
[2] Student's t-test and ANOVA was used to test for differences of imaging biomarkers by the demographic features and imaging biomarkers
[3] Other includes B30s, B41s, B70s, CHST, FC01, FC13, LUNG, and STANDARD
[4] Distribution based on the tertile values Convexity of Tumor Border is Predictive of Patient Survival The convexity of the tumor border was calculated as the ratio of the volumes contained within a) the tumor border (FIG. 12a) to b) the calculated convex hull (FIG. 12a). FIG. 12b demonstrates tumor shape morphology ordered according to the computed mean convexity score. A lower convexity score is reflective of a more irregular shape and expected worse survival. Higher convexity scores described convex shapes with fewer spiculations and irregularities along the boundary. FIG. 12c shows that high (>median) and low convexity separated patients with good and poor overall survival time (p=0.008, log-rank test). Convexity values for this cohort ranged from 0.57 to 0.97, with the median value=0.89.

Entropy Captures the Heterogeneity of the Core and Border Regions of the Tumor

Figure 13:
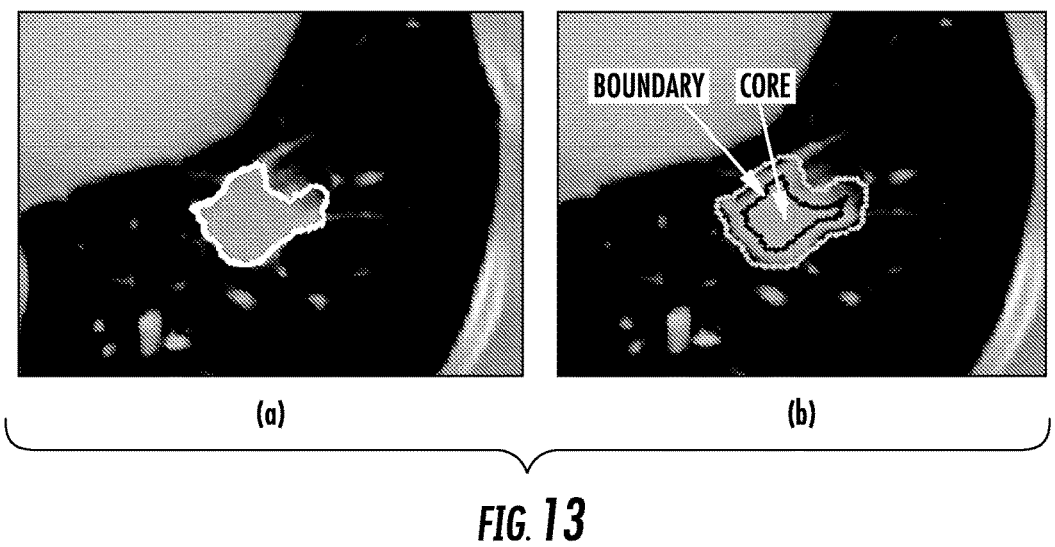
FIG. 13 depicts how (a) the original tumor ROI is (b) subdivided into core and boundary regions in order to assess intratumoral variation of entropy.

Heterogeneity of pixel intensity distributions within the tumor was quantified using an entropy filter. Entropy is a statistical measure of randomness; calculated based on the intensity histogram counts within a sliding window. For each pixel within the tumor ROI, local entropy was computed using its 25 neighboring pixels in the case of a 5×5 kernel. Additionally, tumor growth and interaction with the surrounding microenvironment has been shown to lead to intratumoral changes that can be observable in radiographic scans (Rutman, A. M. and Kuo, M. D. Eur J Radiol. 2009, 70(2), 232-41). Edge effects were observed at the tumor boundary in the Moffitt cohort, possibly stemming from the tumor interfacing with the surrounding environment, resulting in larger changes in intensity values in these regions. Therefore, a spatial constraint was also imposed on the entropy evaluation by using filters for core and boundary regions of the tumor (FIG. 13).

Figure 14:
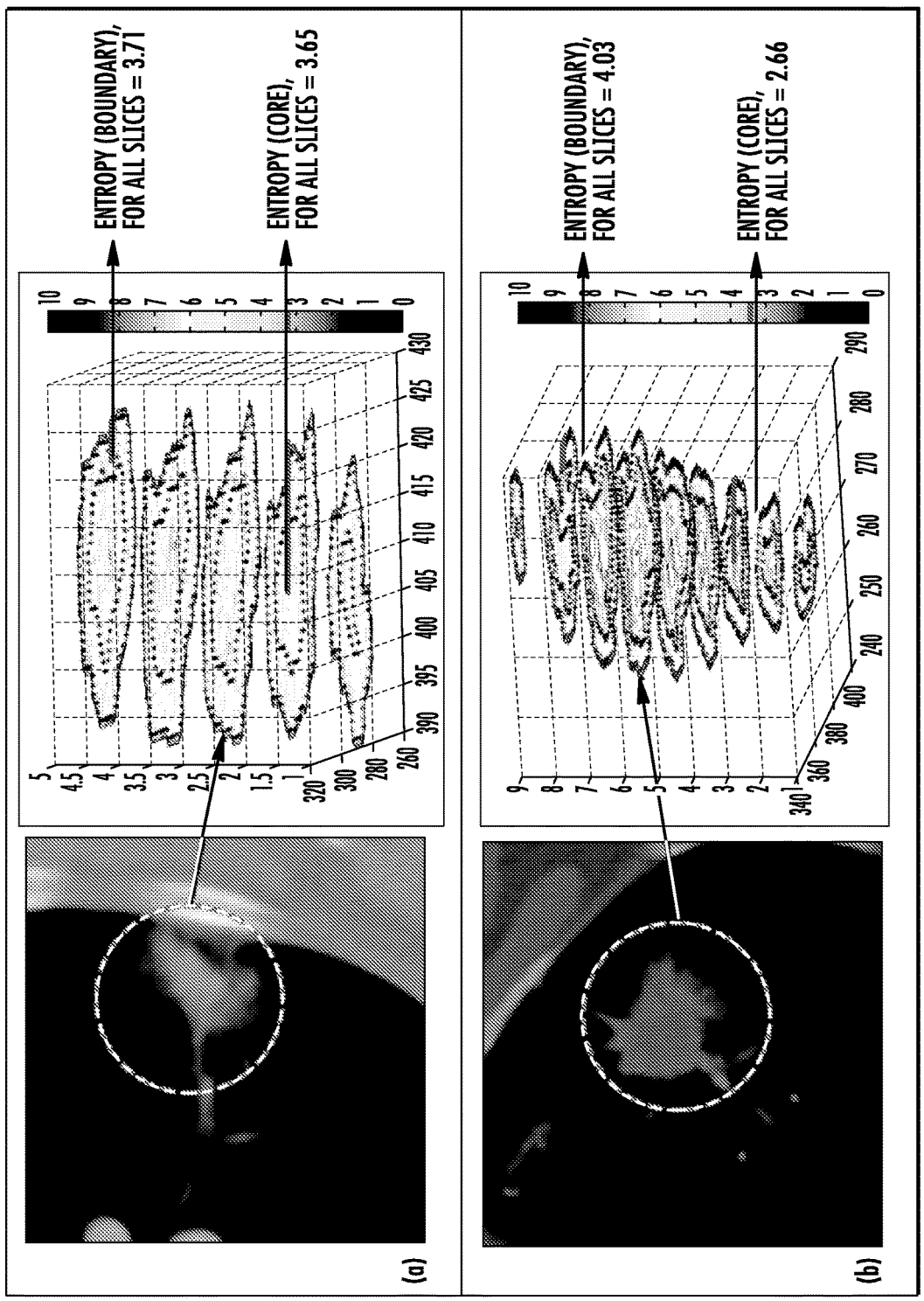
FIG. 14 depicts that while some tumors present with consistent mean entropy across the core and the boundary (top row), others have a distinct difference in the values (bottom row).

FIG. 14 shows contour plots of entropy computed in the boundary and core VOIs, with dotted lines separating the regions along with representative CT scan slices. It was observed that the average entropy within the core and boundary regions of some tumors had similar values (FIG. 14a) whereas, in other tumors, values in the two regions were noticeably different (FIG. 14b). Within the core, the minimum entropy value recorded across all tumors was 1.76, and the maximum entropy value was 4.11. The median entropy value in the core region was 2.83. Entropy in the boundary region ranged from 3.27 (minimum) to 4.26 (maximum), with a median value of 4.00. Based on these differences in entropy, the ratio between the mean core and boundary VOIs for each tumor was computed as an additional imaging feature.

Difference in Entropy Between the Core and Border Regions of the Tumor is Prognostic In all cases, the median entropy value was used to discriminate between low and high entropy groups. Entropy measures for the entire segmented region, ignoring core and boundary regions, were not statistically significant (p=0.28) with respect to overall survival. Evaluating entropy within the boundary region only was also not significant (p=0.96). Furthermore, it appeared that high entropy values in the border region skewed the performance of the feature when calculated across the entire tumor region. Restricting the calculation of entropy to the core region approached statistical significance (p=0.059) in that tumors with high (>median) core entropy tended to yield a worse prognosis. Entropy of the core may capture important intratumoral characteristics such as necrosis and textural heterogeneity. The entropy ratio between the core and boundary subregions was prognostic with respect to survival outcomes (p=0.04, FIG. 15a). Tumors for which the entropy was consistent throughout the core and boundary regions were associated with better survival outcome and tumors presenting with a measurable difference between the core and the boundary regions were correlated with worse prognosis.

Figure 15:
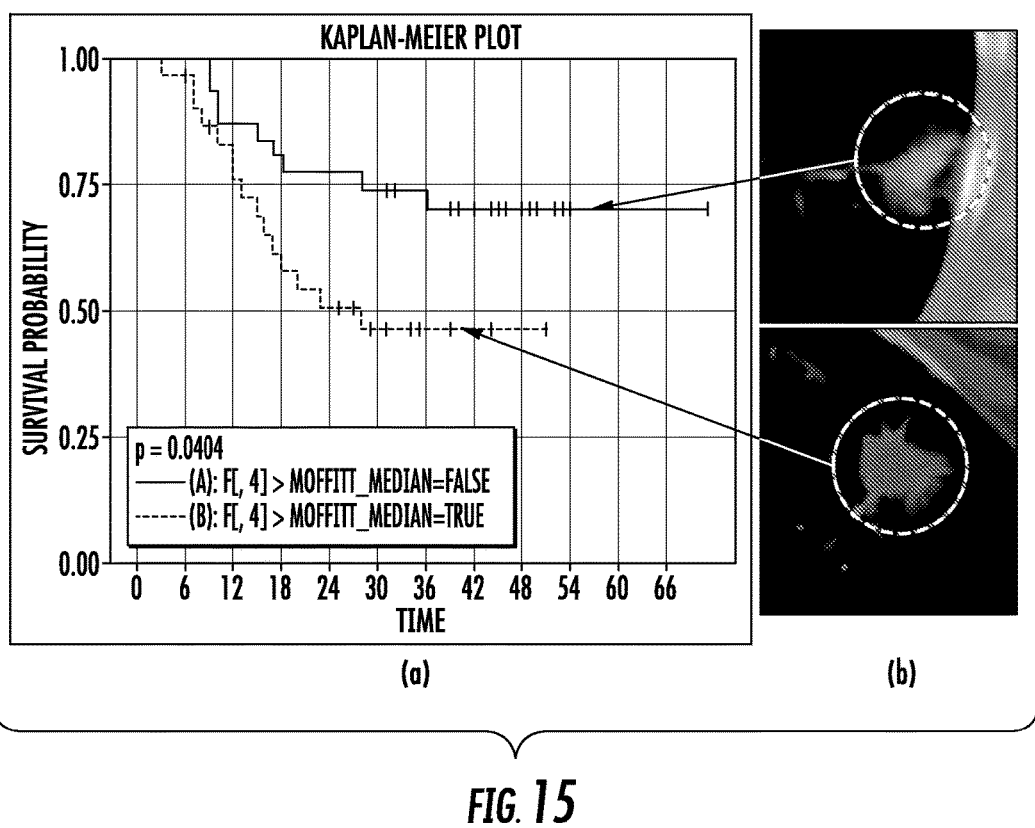
FIG. 15 depicts that the contrast between the core and border regions of the tumor is predictive of patient survival (a). The tumors in the two prognostic groups did not appear significantly different in the CT scans (b).

Representative CT slices of the tumors from the two prognostic groups, as defined by larger than median entropy ratio of the core and boundary VOIs, are shown in FIG. 15b. Within the cohort, the minimum computed ratio between the core and boundary region was equal to 0.94, while maximum ratio of entropies was 2.19. The median entropy ratio for the cohort was 1.41. When visually inspected by experienced radiologists, tumors from these two prognostic groups were not described as being prognostically different. In fact, the tumor at the top in FIG. 15b might be considered to have worse prognosis due to its attachment to the pleural wall, which is a known negative prognostic indicator. In contrast, entropy imaging feature produced an objective and reliable quantification score capable of ordering the tumors along the prognostic spectrum.

Imaging Biomarkers are Independent Prognostic Markers

Differences in these imaging features across prognostic clinical categories of age, gender and clinical stage were tested for, and there were no statistically significant associations (Table 2). Also, correlation between the entropy ratio and convexity (R=0.207) was not observed, suggesting the features capture different aspects of the tumor and may be prognostically independent (Table 3). The features were not correlated to tumor volume (Convexity: R=−0.111 and Entropy: R=0.102). The prognostic importance of the variables together was also examined (Table 4), with both features remaining significant. When adjusting for age, gender and clinical stage, the features remained significant. The higher convexity values were associated with better outcomes (HR=0.31) whereas the higher entropy ratio values were associated with poorer outcomes (HR=2.36).

TABLE 3

Correlation matrix of the imaging features.

|  | Entropy ratio | Tumor volume | Convexity |
|---|---|---|---|
| Entropy ratio | 1.000 | | |
| Tumor volume | 0.102 | 1.000 | |
| Convexity | 0.207 | −0.308 | 1.000 |

TABLE 4

Survival analyses when the imaging features are dichotomized at the median,

|  | uHR (95% CI)[1] | uHR (95% CI)[2] | mHR[1] |
|---|---|---|---|
| Entropy ratio | 2.19 (0.94-5.08) | 2.33 (1.00-5.45) | 2.36 (1.00-5.58) |
| Tumor volume | 2.59 (1.06-6.29) | — | — |
| Convexity | 0.34 (0.14-0.82) | 0.32 (0.13-0.78) | 0.31 (0.12-0.78) |
| Age | — | — | 1.11 (0.44-2.83) |
| Gender | — | — | 1.76 (0.73-4.23) |
| Stage | — | — | 1.45 (0.84-2.49) |

[1]Each imaging biomarker is analyzed independently in an univariate model
[2]Based on forward selection, only two imaging biomarkers are included in the model
[3]Only two imaging biomarkers are included in the model plus age, gender and stage Validation of Prognostic Value with an Independent Cohort In order to further assess the performance of the developed imaging features, feature extraction algorithms were applied to an external imaging cohort, acquired at Maastricht University Medical Center in Maastricht, the Netherlands. The team members of Maastricht Radiation Oncology (MAASTRO) prepared and curated a de-identified cohort of 47 patients diagnosed with lung adenocarcinoma. For each patient, the cohort included CT scans acquired prior to treatment as well as clinical data including demographics, diagnosis, TNM stage, and patient survival. Table 5 shows some of the clinical and imaging characteristics for this cohort of 47 patients with lung adenocarcinoma.

TABLE 5

Distribution of study population demographics and imaging parameters by imaging biomarkers.

| | | | Imaging biomarkers | | | | | |
|---|---|---|---|---|---|---|---|---|
| | | | Entropy ratio | | Tumor volume | | Convexity | |
| Characteristic [1] | No. | (%) | Mean | (SD) | Mean | (SD) | Mean | (SD) |
| Overall | 47 | (100) | 1.27 | (0.16) | 1,576,573 | (5,538,671) | 0.86 | (0.07) |
| Demographics | | | | | | | | |
| Age at diagnosis | | | | | | | | |
| <65 | 19 | (40.4) | 1.29 | (0.17) | 1,600,656 | (5,324,588) | 0.86 | (0.06) |
| ≥65 | 28 | (59.6) | 1.27 | (0.16) | 1,560,231 | (5,776,054) | 0.87 | (0.08) |
| P-value | | | 0.697 | | 0.981 | | 0.725 | |

TABLE 5-continued

Distribution of study population demographics and imaging parameters by imaging biomarkers.

| | | | Imaging biomarkers | | | | | |
| | | | Entropy ratio | | Tumor volume | | Convexity | |
| Characteristic [1] | No. | (%) | Mean | (SD) | Mean | (SD) | Mean | (SD) |
|---|---|---|---|---|---|---|---|---|
| Gender | | | | | | | | |
| Female | 22 | (46.8) | 1.27 | (0.17) | 1,673,242 | (6,449,505) | 0.87 | (0.07) |
| Male | 25 | (53.2) | 1.28 | (0.16) | 1,491,504 | (4,731,241) | 0.87 | 0(.07) |
| P-value | | | 0.847 | | 0.912 | | 0.947 | |
| Stage[1] | | | | | | | | |
| Stage I | 10 | (21.7) | 1.21 | (0.13) | 87,739 | (150,848) | 0.89 | (0.04) |
| Stage II | 21 | (54.7) | 1.35 | (0.18) | 385,901 | (675,387) | 0.89 | (0.05) |
| Stages III and IV | 15 | (32.6) | 1.23 | (0.13) | 4,340,499 | (9,383,981) | 0.82 | (0.09) |
| P-value | | | 0.017 | | 0.067 | | 0.002 | |
| Imaging Parameters | | | | | | | | |
| Voltage, KvP | | | | | | | | |
| 120 | 40 | (85.1) | 1.27 | (0.16) | 1,046,870 | (3,786,242) | 0.87 | (0.07) |
| 130 or 140 | 7 | (14.9) | 1.27 | (0.17) | 4,603,446 | (11,400,000) | 0.86 | (0.09) |
| P-value | | | 0.954 | | 0.118 | | 0.761 | |
| Convolution kernel | | | | | | | | |
| A, B | 23 | (48.9) | 1.27 | (0.13) | 1,486,610 | (4,834,356) | 0.86 | (0.07) |
| B30s, B60f, B70s | 5 | (10.6) | 1.15 | (0.04) | 6,194,466 | (1,3532,86) | 0.85 | (0.10) |
| B40f | 15 | (31.9) | 1.28 | (0.18) | 478,889 | (1,556,613) | 0.88 | (0.06) |
| Other | 4 | (8.5) | 1.47 | (0.19) | 437,803 | (376,848) | 0.88 | (0.06) |
| P-value | | | 0.026 | | 0.24 | | 0.74 | |
| Slice thickness, mm | | | | | | | | |
| <5.0 | 18 | (38.3) | 1.25 | (0.17) | 3,350,823 | (8,667,079) | 0.85 | (0.09) |
| ≥5.0 | 29 | (61.7) | 1.29 | (0.16) | 475,314 | (1,228,994) | 0.88 | (0.06) |
| P-value | | | 0.345 | | 0.084 | | 0.161 | |
| Pixel resolution[4], mm | | | | | | | | |
| <0.9547 | 15 | (31.9) | 1.3 | (0.18) | 2,627,460 | (7,726,859) | 0.86 | (0.07) |
| ≥0.9547 to <0.9766 | 19 | (40.4) | 1.26 | (0.17) | 417,926 | (1,384,700) | 0.88 | (0.07) |
| ≥0.9766 | 13 | (27.7) | 1.26 | (0.14) | 2,057,416 | (6,427,053) | 0.86 | (0.08) |
| P-value | | | 0.672 | | 0.489 | | 0.652 | |

[1] Stage was missing for 1 patient

The CT scans used for the feature extraction had slice thickness ranging between 1.5 mm and 5 mm. CT scans were segmented by the MAASTRO team using the Moffitt segmentation protocol (LuTA for lung delineation and single click ensemble segmentation algorithm for tumor segmentation). Feature extraction algorithms for convexity and entropy calculations were applied to these de-identified segmented CT scans.

Figure 16:
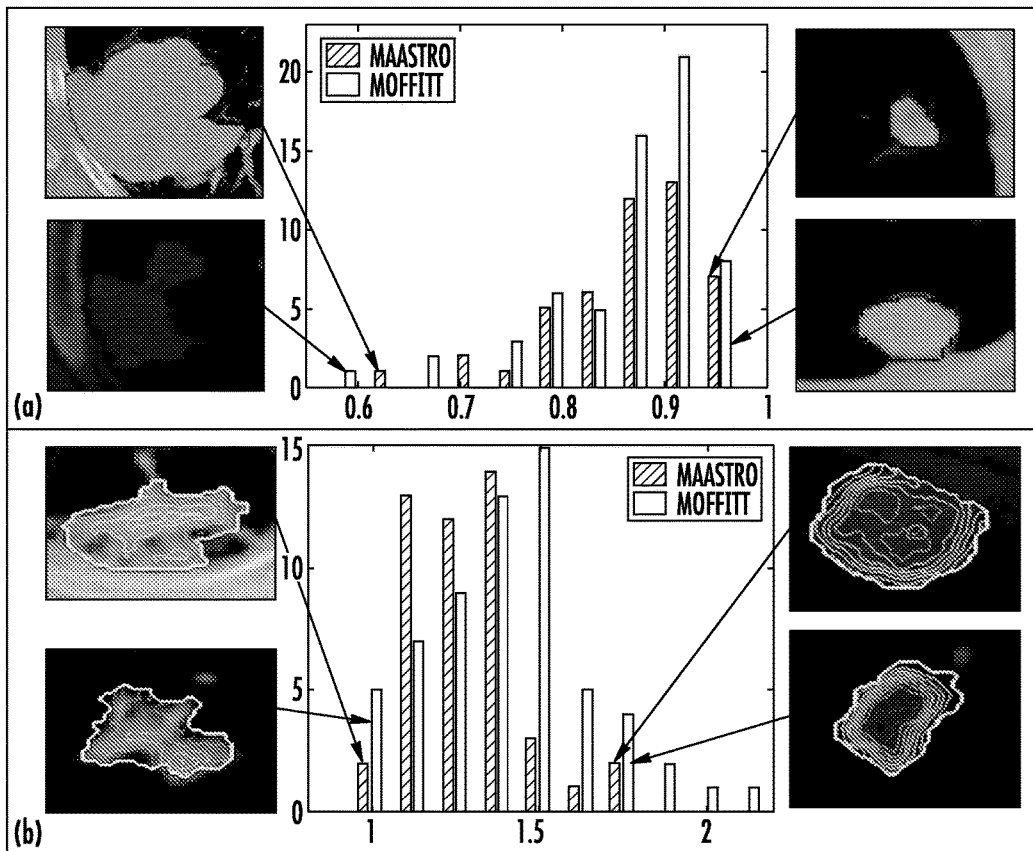
FIG. 16 depicts a histogram of the two imaging features across two cohorts. Convexity (a) shows similar range across the Maastro and Moffitt cohorts. However, the Moffitt cohort is enriched with round tumors. The range of values for the entropy ratio feature (b) is larger in the Moffitt cohort. Both convexity (a) and entropy ratio (b) consistently capture targeted tumor characteristics in both cohorts.

In the first step of the validation, the distribution of the imaging features were compared across the cohorts and confirmed that they indeed described the imaging characteristics of the tumors. The histograms for the convexity and entropy ratio are shown in FIG. 16 for both cohorts together with representative CT scans. FIG. 16a shows that the convexity descriptor has a similar range across the two data sets, but that the Moffitt data set distribution was skewed towards rounder, less spiculated tumor shapes. Consistently, across both cohorts, low convexity scores correspond to more irregular tumor shapes, while high convexity were indicative of rounder, convex shapes with fewer concavities and irregularities along the tumor perimeter. Extreme phenotypes for both cohorts were chosen based on the high (FIG. 16a, right) and low (FIG. 16a, left) convexity scores, to illustrate the performance of the imaging descriptor. FIG. 16b shows that the histogram for entropy ratio was also different between the cohorts. The prevalence of low scores for the Maastro cohort is again the result of clinical characteristics of the cohort, which lead to biological and imaging differences of the tumors. Since entropy coefficients were computed based on intensity values of the pixel VOIs, contour plots were used (FIG. 16b) to visualize differences of the extreme phenotypes, chosen based on the entropy ratio score. Contours are drawn around the homogenous clusters of entropy coefficients thus forming a map of entropy regions. The phenotypes described by the low value entropy ratio (FIG. 16b, left) were similar across both cohorts. The contour plot profile corresponding to high entropy ratio (FIG. 16b, right) appeared consistent for the cohorts, as well.

To evaluate prognostic efficacy of the extracted imaging features in the external cohort, survival analyses were carried out in accordance with the previously applied procedure for Moffitt's patient cohort. Therefore, feature scores derived from the MAASTRO cohort were dichotomized by applying the median values established using the original study cohort of 61 patients from Moffitt (convexity 0.89, and entropy ratio, 1.4), and evaluated using Kaplan-Meier survival curves and the log-rank test. Based on these median splits, neither convexity (p=0.7) nor entropy ratio (p=0.8) features were predictive of survival. However, a different trend was observed when using univariate Cox Proportional Hazards Regression Analysis: convexity scores computed on MAASTRO cohort correlated with survival (p=0.008).

Both the original and the validation datasets were further explored by examining the extreme tumor phenotypes identified based on the distribution of computed tumor scores. Patient survival was compared between two subpopulations, with low (<0.8) and high (>0.9) convexity scores (Moffitt, p=0.07, Maastro, p=0.02). Similarly, two subpopulations were identified using low (<1.23) and high (>1.5) entropy ratio scores. While the difference between these subpopulation was statistically significant for Moffitt dataset (15 patients vs. 19 patients, p=0.04), due to a difference in the range, there were not enough patients in the Maastro dataset to represent the high (>1.5) entropy ratio scores (2 patients).

Figure 17:
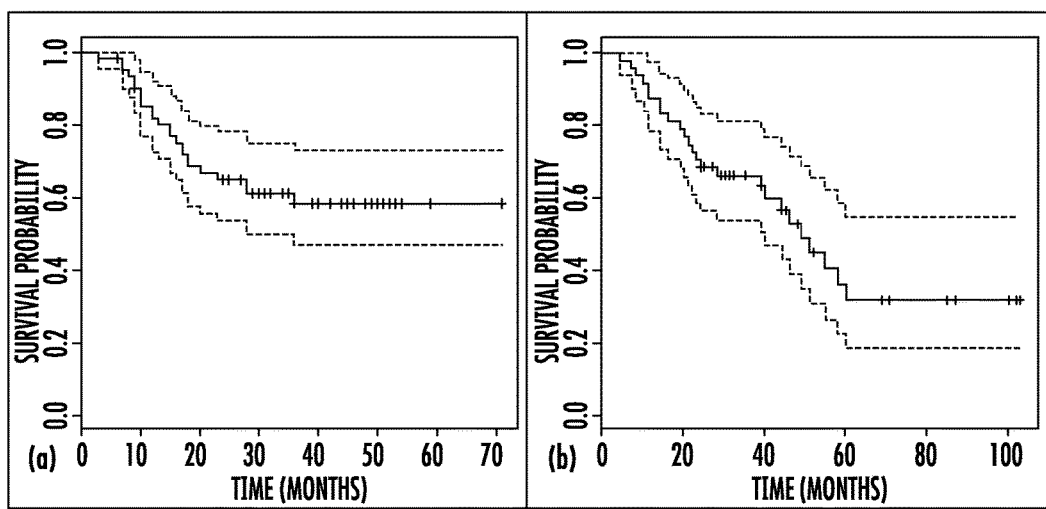
FIG. 17 depicts survival plots for the (a) Moffitt and (b) Maastro cohorts.

The differences in survival analyses are not surprising due to the unique patients' characteristics which manifest themselves in the differences in the distribution of tumor scores. While patients in the Moffitt cohort were surgical candidates, predominantly stages I and II, the MAASTRO cohort consisted of radiotherapy planning patients with more advanced stages of lung cancer. Furthermore, the overall survival trend for the cohorts differed (FIG. 17). The Moffitt cohort (FIG. 17a) had an overall better survival rate than the the Maastro cohort (FIG. 17b), which had only approximately 30% of the patients living past 60 months. It is however noteworthy that both features were able to consistently score the tumors in either cohort according to their shape and density variation.

DISCUSSION

Tumors are complex evolving systems that are continuously changing as a result of internal processes and the interaction with the surrounding environment. BI-RADS lexicon, developed for breast imaging reporting, has illustrated that both morphologic and intratumoral imaging characteristics are critical in breast cancer diagnosis (Jia, G et al. *Radiology*. 2008, 248(3), 901-9). Further, metabolic changes and evolutionary processes can be reflected intratumoraly and lead to morphological changes. The changes on the molecular level eventually extend to more observable level and manifest themselves as, e.g., regions of necrosis, hemorrhage and vascularization, which are observable in CT scans. On the other hand, tumor microenvironment plays an important role in tumor progression and response to therapy. Interaction with the surrounding anatomy combined with the proliferation and growth rates impacts the morphology of the tumor region, which cannot be adequately summarized by solely quantifying intratumoral textural characteristics. Therefore, two distinct phenomena for imaging feature development were pursued: intratumoral changes within tumor VOI and the interaction of the tumor region with the surrounding environment inferred from tumor shape. The convexity feature quantified tumor morphology and the presence of spiculations along the perimeter. Entropy was used to quantify density variations within tumor core and boundary regions.

NSCLC tumors can be characterized, using diagnostic imaging, based on their size, shape and margin morphology, and extent of internal enhancement and necrosis. However, the terminology used in radiology to characterize the pathological findings remains subjective. To date, imaging features are generally derived from a single slice and rely on distributional summary statistics. Averaging the values across the ROI cannot adequately quantify the range of intensity values as well as the importance of their spatial distribution (Graves, EE; Maity, A; Le, Q T. *Semin Radiat Oncol*. 2010, 20(3), 156-63). In order to introduce a spatial component, each segmented tumor region was subdivided into core and boundary regions. This allowed the edge effect to be accounted for, where larger changes in texture and intensities occur at the tumor-environment interface, and to introduce an additional spatial component into the intratumoral quantification. While this approach is not truly three-dimensional, it provides a pragmatic compromise in the presence of clinical variability, most notably variable slice thickness across patients.

Variability across sets of CT scans can exist even when a standardized image acquisition protocol is established prior to the data collection. For example, variations in tube voltage across different CT systems and adjustments made based on the size of the patient will result in slightly different CT scans. Although this variability can be a limitation in some studies, ultimately for the computed tomographic biomarkers to be adopted into clinical practice and utilized across multiple imaging centers, these biomarkers must be stable in the presence of image acquisition variability. The features developed herein were intended, in part, to be robust to these challenges.

Cohort size in retrospective studies is often limited and further reduced by the curation of clinical and imaging data. In order to avoid data sparsity, it is important to keep the number of imaging features reasonably low and reflective of the cohort. In order to adequately relay tumor characteristics while coping with dimensionality restrictions, preference should be given to hypothesis driven feature derivation predicated on available biomarkers and tumor biology associations. Likewise, validation of imaging features derived from prospectively assembled cohorts presents an interesting challenge as the field continues to mature. It is essential to refute spurious findings by validating imaging features in independent, previously unseen cohorts. However, the lack of a 'golden standard' for testing derived features is often coupled with a number of confounding factors stemming from imaging variability and heterogeneity within patient cohort. It is therefore important to recognize that differences in patient population, quality and manner of data acquisition and subsequent processing can result in validation cohorts that are not adequate for fair assessment. Care should hence be taken not to discard potentially significant imaging features based on the validation study alone. This highlights the significance and merits of hypothesis driven imaging feature design predicated upon recognized biological associations, as these associations can serve as additional validation criteria in an independent cohort.

The aim of this study was to develop objective and systematic quantitative computed tomographic imaging features that were predictive of patient survival. The development of these imaging features was hypothesis driven, as it was pursued to quantify the semantic descriptors employed by radiologists. The results suggest that quantitative imaging features could be used as an additional prognostic tool in management of lung adenocarcinomas. Although more work is needed to determine clinical utility, it is clear that these imaging features are capable of quantifying key tumor characteristics. Capturing details of the biological activity of the tumor through minimally-invasive imaging techniques can inform precision medicine strategies longitudinally where serial biopsies may be too difficult to achieve. Imaging features, combined with RECIST measurements and laboratory test results, can in the future be the de facto standard of a decision support system employed to personalize and optimize treatment protocols.

CONCLUSIONS

Two computed tomographic imaging features were developed that quantify shape and texture variations within lung tumors. It was quantitatively demonstrated in 61 diagnostic CT studies of NSCLC patients that the developed imaging features are capable of classifying patients based on CT scans alone into two prognostic categories within statically significant bounds. The development of prognostic imaging features capable of describing key biological characteristics while being robust and stable despite the inherent variability of diagnostic CT data was focused on. The convexity feature consistently and quantitatively differentiated between irregular and spiculated and convex tumor shapes. To quantify the texture variations across the lesion, a spatial component was introduced by subdividing the segmented region into core and boundary sub-regions. Entropy filtering was applied and the overall lesion density was evaluated by comparing the textures of the core and boundary sub-regions. For both imaging features, the calculations were extended across all CT scans containing segmented tumor region. Using survival analysis, it was shown that the derived imaging features, convexity and entropy ratio, were prognostic of patient survival, with a log rank P values of 0.008 and 0.04, respectively.

An independent cohort of 47 primarily lung adenocarcinoma patients was used for validation. Due to the differences in clinical characteristics and imaging parameters, these imaging features were not predictive of survival when tested in accordance with the originally established testing criteria. However, the developed imaging features systematically scored the tumors according to their pursued characteristics (speculation of the boundary and intratumoral density variation). Furthermore, extreme tumor phenotypes were identified based on the distribution of tumor scores and exhibited survival differences.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for quantitatively predicting the severity of a tumor in a subject, comprising
    receiving, using a processor, an anatomical image acquired from a region of interest in a subject containing the tumor, wherein the anatomical image is a computed tomography (CT) image;
    segmenting, using the processor, the anatomical image using a segmentation algorithm to define a volume of interest representing the tumor, thereby generating a segmented image of the tumor;
    extracting, using the processor, one or more image features from the segmented image of the tumor, wherein the one or more image features are selected from the group consisting of entropy or a combination of convexity and entropy;
    generating a quantitative score for the one or more image features, using the processor, wherein the quantitative score for the one or more image features is associated with tumor severity, and wherein the quantitative score for entropy is a ratio of the average entropy in a core region of the segmented image of the tumor to the average entropy in a boundary region of the segmented image of the tumor; and
    presenting, using the processor, the quantitative score to a user for selecting a course of therapy for the subject based on the quantitative score for the one or more image features.

2. The method of claim 1, wherein the one or more image features is entropy.

3. The method of claim 1, wherein the ratio is calculated by an algorithm that performs steps comprising:
    a) subdividing the segmented image of the tumor into the core region and the boundary region;
    b) calculating an entropy coefficient for each pixel in the core region and the boundary region;
    c) averaging the entropy coefficients for the core region and for the boundary region; and
    d) comparing the average entropy coefficient of the core region to the average entropy coefficient of the boundary region to obtain the entropy ratio.

4. The method of claim 1, wherein the one or more image features further comprises convexity.

5. The method of claim 4, wherein the convexity is calculated by an algorithm that performs steps comprising:
    a) identifying a border of the segmented image of the tumor;
    b) creating a mask of the segmented image of the tumor;
    c) calculating the area of the mask of the segmented image of the tumor;
    d) creating a convex hull of the border of the segmented image of the tumor;
    e) calculating the area of the convex hull; and
    f) comparing the area of the mask to the area of the convex hull to calculate convexity.

6. The method of claim 5, wherein the algorithm for convexity further comprises correcting for overlap with a structure comprising:
    a) identifying a border of a structure;
    b) comparing the border of the structure with the border of the segmented image of the tumor to determine overlap between the segmented image of the tumor and the structure; and
    c) eliminating overlapping regions from the area of the mask of the segmented image of the tumor and the area of the convex hull used to calculate convexity.

7. The method of claim 1, wherein the tumor comprises non-small cell lung cancer.

8. The method of claim 7, wherein the tumor is a lung adenocarcinoma.

9. The method of claim 1, wherein the method is combined with a tumor node metastasis (TNM) staging system to predict the severity of the tumor.

10. The method of claim 1, wherein the anatomical image comprises a stack of two-dimensional image slices of the region of interest.

11. The method of claim 10, wherein the method further comprises rendering the two-dimensional image slices into a three-dimensional image.

12. The method of claim 10, wherein the wherein the quantitative score for convexity is calculated as the average convexity for each two-dimensional image slice.

13. The method of claim 1, further comprising the step of acquiring the anatomical image of the region of interest in the subject containing the tumor.

14. The method of claim 1, further comprising selecting a course of therapy for the subject based on the quantitative score for the one or more image features.

15. The method of claim 14, wherein the quantitative score for convexity is an indication of either an irregular or a convex tumor shape, wherein the method comprises selecting adjuvant therapy for the subject if the quantitative score for convexity indicates an irregular tumor shape.

16. The method of claim 14, wherein the quantitative score for entropy is an indication of tumor density, wherein the method comprises selecting adjuvant therapy for the subject if the quantitative score for entropy indicates a high tumor density.

17. A method of selecting a course of therapy for a subject based on the severity of a tumor in the subject, the method comprising:
receiving a quantitative score for one or more image features extracted from a segmented image of the tumor, wherein:
the quantitative score for the one or more image features is associated with tumor severity and the tumor comprises non-small cell lung cancer,
the one or more image features are selected from the group consisting of entropy or a combination of convexity and entropy,
the quantitative score for entropy is an indication of tumor density and is a ratio of the average entropy in a core region of the segmented image of the tumor to the average entropy in a boundary region of the segmented image of the tumor, and
the quantitative score for convexity is an indication of either an irregular tumor shape or a convex tumor shape; and
selecting a course of therapy for the subject based on the quantitative score for the one or more image features, wherein:
when the quantitative score for entropy indicates a high tumor density, the method comprises selecting surgery and post-surgery adjuvant therapy for the subject,
when the quantitative scope for entropy does not indicate a high tumor density, the method comprises selecting surgery for the subject,
when the quantitative score for convexity indicates an irregular tumor shape, the method comprises selecting surgery and post-surgery adjuvant therapy for the subject, and
when the quantitative score for convexity indicates a convex tumor shape, the method comprises selecting surgery for the subject.

* * * * *

UNITED STATES PATENT AND TRADEMARK OFFICE
CERTIFICATE OF CORRECTION

PATENT NO. : 10,339,648 B2  
APPLICATION NO. : 14/761688  
DATED : July 2, 2019  
INVENTOR(S) : Olya Stringfield et al.

Page 1 of 1

It is certified that error appears in the above-identified patent and that said Letters Patent is hereby corrected as shown below:

In the Specification

At Column 4, Line 57, delete the text "leaming" and replace it with --learning--.

Signed and Sealed this
Twentieth Day of October, 2020

Andrei Iancu
*Director of the United States Patent and Trademark Office*